(12) United States Patent
Nagamine et al.

(10) Patent No.: US 11,414,923 B2
(45) Date of Patent: Aug. 16, 2022

(54) LIGHT-SHIELDING DEVICE AND LIGHT-SHIELDING METHOD

(71) Applicant: SONY CORPORATION, Tokyo (JP)

(72) Inventors: Kunihiko Nagamine, Kanagawa (JP); Junichi Rekimoto, Kanagawa (JP); Shunichi Suwa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 629 days.

(21) Appl. No.: 16/328,716

(22) PCT Filed: Sep. 14, 2017

(86) PCT No.: PCT/JP2017/033202
§ 371 (c)(1),
(2) Date: Feb. 26, 2019

(87) PCT Pub. No.: WO2018/061791
PCT Pub. Date: Apr. 5, 2018

(65) Prior Publication Data
US 2019/0195012 A1    Jun. 27, 2019

(30) Foreign Application Priority Data
Sep. 27, 2016  (JP) .............................. JP2016-187820

(51) Int. Cl.
*E06B 9/24* (2006.01)
*A61M 21/00* (2006.01)
(Continued)

(52) U.S. Cl.
CPC ................ *E06B 9/24* (2013.01); *A61B 5/002* (2013.01); *A61B 5/0088* (2013.01); *A61B 5/16* (2013.01);
(Continued)

(58) Field of Classification Search
CPC ........ A61M 2230/005; A61M 2230/06; A61M 2230/30; A61M 2230/42; A61M 2230/50;
(Continued)

(56) References Cited

U.S. PATENT DOCUMENTS 9,474,876 B1 * 10/2016 Kahn ................... A61B 5/4812
9,535,307 B2 * 1/2017 Rekimoto .......... G06K 9/00255
(Continued)

FOREIGN PATENT DOCUMENTS

CN    104428474 A    3/2015
CN    106662763 A    5/2017
(Continued)

OTHER PUBLICATIONS

Jun Rekimoto "Squama: Modular Visibility Control of Walls and Windows for Programmable Physical Architectures", 04 pages.
(Continued)

*Primary Examiner* — Quan Zhen Wang
*Assistant Examiner* — Rajsheed O Black-Childress
(74) *Attorney, Agent, or Firm* — Chip Law Group

(57) ABSTRACT

The present technology relates to a light-shielding device and a light-shielding method which make an object that is meant to be invisible to human beings enter a state in which the object is hidden so as to be invisible to eyes, or make an object that is meant to be visible enter a state in which the object is visible to eyes in correspondence with biological information. A light-shielding wall, which partitions two spaces and includes a plurality of panels capable of being controlled to a transmitting state in which light is transmitted or a light-shielding state in which light is shielded, is used as a window, an orientation of a face of a user who is sleeping is detected as biological information, and the light-
(Continued)

shielding wall is controlled so that the user is capable of visually recognizing light when it reaches an alarm setting time.

19 Claims, 21 Drawing Sheets

(51) Int. Cl.
*A61B 5/16* (2006.01)
*G02F 1/13* (2006.01)
*E04B 2/74* (2006.01)
*A61B 5/00* (2006.01)
*G06V 40/10* (2022.01)
*G04G 11/00* (2006.01)

(52) U.S. Cl.
CPC ............. *A61B 5/746* (2013.01); *A61M 21/00* (2013.01); *E04B 2/74* (2013.01); *G02F 1/13* (2013.01); *G06V 40/10* (2022.01); *G04G 11/00* (2013.01)

(58) Field of Classification Search
CPC .............. A61M 2230/63; A61M 21/00; A61M 21/0094; A61B 2505/01; A61B 5/002; A61B 5/0077; A61B 5/0088; A61B 5/1176; A61B 5/16; A61B 5/486; A61B 5/6898; A61B 5/746; B21C 47/34; B65H 2701/37; B65H 49/34; E04B 2/74; E06B 9/24; G02F 1/13; Y02B 80/00
See application file for complete search history.

(56) References Cited

U.S. PATENT DOCUMENTS

| 2015/0160528 A1 | 6/2015 | Rekimoto |
| 2015/0354789 A1 | 12/2015 | Paolini |
| 2019/0239757 A1* | 8/2019 | Berkey ................ A61B 5/0004 |
| 2019/0346701 A1* | 11/2019 | Lam ................... G06K 9/00288 |

FOREIGN PATENT DOCUMENTS

| EP | 2873780 A1 | 5/2015 |
| JP | 2000-280896 A | 10/2000 |
| JP | 2002-067690 A | 3/2002 |
| JP | 3188376 U | 12/2013 |
| JP | 3188376 U | 1/2014 |
| WO | 2014/010498 A1 | 1/2014 |
| WO | 2015/191597 A1 | 12/2015 |

OTHER PUBLICATIONS

Jun Rekimoto, "Squama: Modular Visibility Control of Walls and Windows for Programmable Physical Architectures", Proceedings of the International Working Conference on Advanced Visual Interfaces, May 2012, pp. 168-171.

International Search Report and Written Opinion of PCT Application No. PCT/JP2017/033202, dated Nov. 21, 2017, 08 pages of ISRWO.

Jun Rekimoto, "Squama: Modular Visibility Control of Walls and Windows for Programmable Physical Architectures", 4 Pages.

* cited by examiner

LIGHT-SHIELDING DEVICE AND LIGHT-SHIELDING METHOD

CROSS REFERENCE TO RELATED APPLICATIONS

This application is a U.S. National Phase of International Patent Application No. PCT/JP2017/033202 filed on Sep. 14, 2017, which claims priority benefit of Japanese Patent Application No. JP 2016-187820 filed in the Japan Patent Office on Sep. 27, 2016. Each of the above-referenced applications is hereby incorporated herein by reference in its entirety.

TECHNICAL FIELD

The present technology relates to a light-shielding device, a light-shielding method, and a program, and more particularly, to a light-shielding device, a light-shielding method, and a program which make an object that is meant to be invisible enter a state in which the object is hidden so as to be invisible to eyes or is less likely to be visible to eyes, or make an object that is meant to be visible enter a state in which the object is likely to be visible to eyes in correspondence with biological information.

BACKGROUND ART

A light-shielding device that makes an object that is meant to be visible to human beings be visible while hiding an object that is meant to be invisible to human beings is proposed (refer to Patent Document 1).

CITATION LIST

Patent Document

Patent Document 1: International Publication No. 2014/010498

SUMMARY OF THE INVENTION

Problems to be Solved by the Invention

However, the light-shielding device described in Patent Document 1 does not have a configuration of making an object that is meant to be invisible to human beings enter a state in which the object is hidden so as to be invisible to eyes or making an object that is meant to be visible enter a state in which the object is visible to eyes in correspondence with biological information or external information.

The present disclosure has been made in consideration such situations, and an object thereof is to make an object that is meant to be invisible enter a state in which the object is hidden so as to be invisible to eyes or is less likely to be visible to eyes, or to make an object that is meant to be visible enter a state in which the object is likely to be visible to eyes in correspondence with biological information or external information.

Solutions to Problems

According to an aspect of the present disclosure, there is provided a light-shielding device including: a light-shielding wall that partitions a first space and a second space and includes a plurality of regions capable of being controlled to a transmitting state in which light is transmitted or a light-shielding state in which light is shielded; a light-shielding and transmitting information generation unit that generates light-shielding and transmitting information for controlling the transmitting state or the light-shielding state of a position of each of the plurality of regions on the basis of biological information of a user; and a control unit that controls the transmitting state or the light-shielding state of the plurality of regions of the light-shielding wall on the basis of the light-shielding and transmitting information generated by the light-shielding and transmitting information generation unit.

The light-shielding wall may be a window that separates an interior and an exterior, the light-shielding device may further include a biological information acquisition unit that acquires biological information indicating whether or not the user is sleeping in an interior, and the light-shielding and transmitting information generation unit may generate light-shielding and transmitting information for controlling the transmitting state or the light-shielding state of the position of each of the plurality of regions to irradiate a specific position of the interior with light from a light source that exists in the exterior on the basis of whether or not the user is sleeping which is acquired by the biological information acquisition unit.

The biological information may further include information indicating an orientation of a user's face in sleep, and in a case where the user sets an alarm time as an alarm, the light-shielding and transmitting information generation unit may generate light-shielding and transmitting information for controlling the transmitting state or the light-shielding state of the position of each of the plurality of regions on the basis of the orientation of the user's face in sleep on the basis of the biological information so that the user's eyes located at the specific position of the interior are irradiated with light of which a light source is the sun, which is light from the light source that exists in the exterior, at the alarm time.

The biological information may further include information for obtaining a sleep state of the user, the light-shielding device may further include a solar light incident angle calculation unit that calculates an incident angle of light, which is incident to each of the regions of the light-shielding wall and of which a light source is the sun, as a solar light incident angle on the basis of information of latitude and longitude as a position of the solar light incident angle calculation unit, an orientation of the light-shielding wall, and time information, and a degree-of-sleep-depth calculation unit that determines whether or not the user is sleeping at time near the alarm time on the basis of biological information that indicates whether or not the user is sleeping in the interior and is used to obtain a sleep state of the user, and further obtains an easily waking-up time at which the depth of sleep is shallow in a case where it is determined that the user is sleeping, and the light-shielding and transmitting information generation unit may generate light-shielding and transmitting information for controlling the transmitting state or the light-shielding state of a position of each of the plurality of regions on the basis of biological information that is information indicating the orientation of the user's face in sleep, and the solar light incident angle information so that the user's eyes are irradiated with light of which a light source is the sun at easily waking-up time which corresponds to the alarm time and at which the depth of sleep is shallow.

The biological information for obtaining the sleep state of the user includes information of a pulse rate, a body temperature, a blood pressure, a breathing frequency, and a body turning frequency of the user.

The light-shielding device may further include an image capturing unit that captures an image of the user who is sleeping. The biological information acquisition unit may acquire information of the body turning frequency as the biological information as the biological information on the basis of the image captured by the image capturing unit.

The light-shielding device may further include an external information acquisition unit that acquires external information; and a waking-up detection unit that detects waking-up of the user after the alarm time on the basis of biological information for obtaining a sleep state of the user. In a case where waking-up is detected after the alarm time by the waking-up detection unit, the light-shielding and transmitting information generation unit may generate light-shielding and transmitting information for controlling the transmitting state or the light-shielding state of a position of each of the plurality of regions so that the user is capable of visually recognizing display based on the external information.

The external information acquisition unit may acquire external information including rainfall data based on the amount of rainfall that is measured by a rainfall sensor, or PM 2.5 data that is a measurement amount of PM 2.5 that is measured by a PM 2.5 measuring device, and in a case where waking-up is detected by the waking-up detection unit, the light-shielding and transmitting information generation unit may generate light-shielding and transmitting information for controlling the transmitting state or the light-shielding state of the position of each of the plurality of regions on the basis of an orientation of the user's face so that the user is capable of visually recognizing display corresponding to measurement results which correspond to the rainfall data and the PM 2.5 data as the external information.

The light-shielding and transmitting information generation unit may generate light-shielding and transmitting information for controlling the transmitting state or the light-shielding state of the position of each of the plurality of regions so that the user is capable of visually recognizing the display based on the external information at a position on the light-shielding wall at which light from a light source that exists in the exterior does not become backlight for the user.

The light-shielding device may further include an abnormality determination unit that determines whether or not the external information indicates an abnormal state. In correspondence with a determination by the abnormality determination unit as to whether or not the external information is abnormal, the light-shielding and transmitting information generation unit may generate light-shielding and transmitting information for controlling the transmitting state or the light-shielding state of the position of each of the plurality of regions so that the display based on the external information is displayed on the light-shielding wall at a different position or in a different size.

The light-shielding device may further include a transmittance setting unit that sets a transmittance in the plurality of regions controlled to the transmitting state in the light-shielding and transmitting information on the basis of the solar light incident angle information so as to adjust a light quantity of light of which a light source is the sun that is visually recognized by the user, and adds the transmittance to the light-shielding and transmitting information.

The light-shielding device may further include a biological information acquisition unit that acquires biological information indicating initiation of a predetermined activity of the user. The light-shielding and transmitting information generation unit may generate light-shielding and transmitting information for controlling the transmitting state or the light-shielding state of a position of each of the plurality of regions so that the user is capable of visually recognizing an elapsed time from timing at which the predetermined activity of the user, which is acquired by the biological information acquisition unit, is initiated.

The biological information acquisition unit may acquire biological information indicating initiation of brushing of teeth as the biological information indicating that the predetermined activity of the user is initiated, and the light-shielding and transmitting information generation unit may generate light-shielding and transmitting information for controlling the transmitting state or the light-shielding state of the position of each of the plurality of regions so that the user is capable of visually recognizing an elapsed time from timing at which brushing of teeth of the user is initiated and which is acquired by the biological information acquisition unit in a shape that resembles a sandglass.

The light-shielding device may further include an image capturing unit that captures an image of a user; and a charging stand of an electric toothbrush that is used in brushing of teeth of the user. The biological information acquisition unit may determine whether or not the user grips the toothbrush in an image that is captured by the image capturing unit, may determine whether or not the electric toothbrush is connected to the charging stand and is capable of being charged, and may acquire biological information indicating initiation of the brushing of teeth in at least one of a case where the electric toothbrush is gripped by the user, and a case where the electric toothbrush is not connected to the charging stand and is not capable of being charged in the image on the basis of the determination result.

The first space may be an interior, the second space may be an exterior, and the light-shielding wall may be a wall that separates the interior and the exterior. The light-shielding device may further include a biological information acquisition unit that acquires the height of a person who exists in the exterior as biological information. The light-shielding and transmitting information generation unit may generate light-shielding and transmitting information for controlling the entirety of the plurality of regions to a light-shielding state at an initiation time of a usable time of the interior. The light-shielding and transmitting information generation unit may generate light-shielding and transmitting information for controlling the plurality of regions higher than the height among the plurality of regions in the light-shielding wall to the transmitting state on the basis of information of the height of a person which is acquired by the biological information acquisition unit at time previous to an expiration time of the interior usable time by a predetermined time.

After the time that is previous to the expiration time of the interior usable time by a predetermined time, the light-shielding and transmitting information generation may generate light-shielding and transmitting information for controlling the plurality of regions, which are higher than the height and are controlled to a light-shielding state in the light-shielding wall, among the plurality of regions to the transmitting state in a time series and gradually in an order from the plurality of regions of the highest partial region on the basis of the information of the height of a person which is acquired by the biological information acquisition unit.

At the expiration time of the interior usable time, the light-shielding and transmitting information generation unit may generate light-shielding and transmitting information for controlling the entirety of the plurality of regions to the transmitting state.

The interior may include a conference room, and an interior of a room that is paid by the hour.

According to another aspect of the present disclosure, there is provided a light-shielding method of a light-shielding device including a light-shielding wall that partitions a first space and a second space and includes a plurality of regions capable of being controlled to a transmitting state in which light is transmitted or a light-shielding state in which light is shielded. The method includes steps of: generating light-shielding and transmitting information for controlling the transmitting state or the light-shielding state of a position of each of the plurality of regions on the basis of biological information of a user; and controlling the transmitting state or the light-shielding state of the plurality of regions of the light-shielding wall on the basis of the light-shielding and transmitting information that is generated.

According to still another aspect of the present disclosure, there is provided a program that allows a computer to function as: a light-shielding wall that partitions a first space and a second space and includes a plurality of regions capable of being controlled to a transmitting state in which light is transmitted or a light-shielding state in which light is shielded; a light-shielding and transmitting information generation unit that generates light-shielding and transmitting information for controlling the transmitting state or the light-shielding state of a position of each of the plurality of regions on the basis of biological information of a user; and a control unit that controls the transmitting state or the light-shielding state of the plurality of regions of the light-shielding wall on the basis of the light-shielding and transmitting information generated by the light-shielding and transmitting information generation unit.

According to the aspects of the present disclosure, the first space and the second space are separated by the light-shielding wall including the plurality of regions capable of being controlled to the transmitting state in which light is transmitted or the light-shielding state in which light is shielded. The light-shielding and transmitting information for controlling the transmitting state or the light-shielding state of the position of each of the plurality of regions is generated on the basis of the biological information of a user. The transmitting state or the light-shielding state of the plurality of regions of the light-shielding wall is controlled on the basis of the light-shielding and transmitting information that is generated.

Effects of the Invention

According to the aspects of the present disclosure, it is possible to make an object that is meant to be invisible enter a state in which the object is hidden so as to be invisible to eyes or is less likely to be visible to eyes, or to make an object that is meant to be visible enter a state in which the object is likely to be visible to eyes in correspondence with biological information.

MODE FOR CARRYING OUT THE INVENTION

Figure 1:
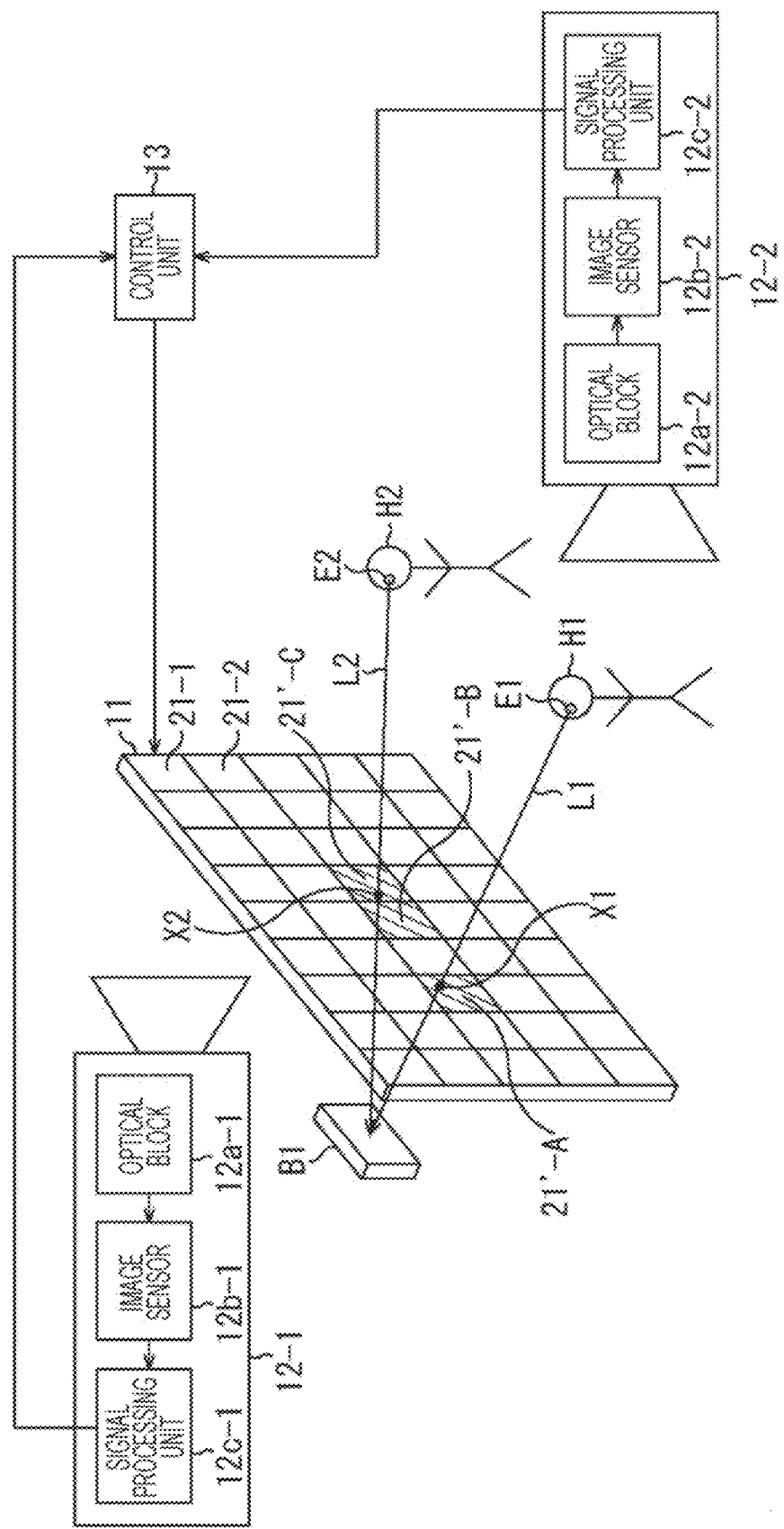
FIG. 1 is a view illustrating an overview of a light-shielding device according to the present disclosure.

Preferred embodiments of the present disclosure will be described in detail with reference to the accompanying drawings. Furthermore, in this specification and the drawings, the same reference numeral will be given to constituent elements having substantially the same functional configuration, and redundant description will be omitted.

Hereinafter, modes (hereinafter, referred to as "embodiments") for carrying out the invention will be described. Furthermore, description will be made in the following order.

1. Overview of Light-Shielding Device of Present Disclosure

2. First Embodiment (example in a case of allowing a user to comfortably wake up on the basis of biological information)

3. Second Embodiment (example in a case of displaying information after waking up on the basis of biological information)

4. Third Embodiment (example in a case of displaying emergent information)

5. Fourth Embodiment (example in a case of displaying a timer on the basis of biological information)

6. Fifth Embodiment (example in a case of displaying a conference-room remaining time on the basis of biological information)

1. Overview of Light-Shielding Device of Present Disclosure

A light-shielding device of the present disclosure is configured to make an object that is meant to be invisible enter a state in which the object is hidden so as to be invisible to eyes or is less likely to be visible to eyes, or to make an object that is meant to be visible enter a state in which the object is likely to be visible to eyes in correspondence with biological information of a user.

More specifically, as illustrated in FIG. 1, the light-shielding device of the present disclosure includes a light-shielding wall 11 that partitions a first space on the left in the drawing and a second space on the right in the drawing, and includes a plurality of panels 21 capable of being controlled to a light-shielding state, a transmitting state, or states of being changed to various transmittances. Furthermore, description will be made on the assumption that the panels 21 can be switched to any one state between two states of the light-shielding state and the transmitting state for explanation of an overview of the light-shielding device, and simplification of the explanation, but the panels 21 can also be controlled to states of being changed to various transmittances. Furthermore, the light-shielding state is a state of shielding light even at apart, the transmitting state is a state of transmitting incident light even at a part, and the light-shielding state may be a state in which a transmittance of incident light is lower in comparison to at least the transmitting state. Accordingly, for example, a transmittance of the panels 21 in the light-shielding state may be lower than a transmittance of a panel state in the transmitting state, and the transmittance of the light-shielding state may be 10% to 30% in addition to 0%, and the transmittance of the transmitting state may be 90% to 70% in addition to 100%.

For example, the light-shielding wall 11 controls only panels 21 in a region capable of directly viewing an object B1 that exists in the first space from visual points of persons H1 and H2 who exist in the second space in the light-shielding state, and controls panels 21 in the other regions in the transmitting state. That is, the light-shielding device illustrated in FIG. 1 makes an object, which is not meant to be visible, be invisible.

More specifically, the light-shielding device illustrated in FIG. 1 includes the light-shielding wall 11, cameras 12-1 and 12-2, and a control unit 13. The light-shielding wall 11 partitions the first space that is shown at the left portion in the drawing, and the second space that is shown at the right portion in the drawing. As illustrated in FIG. 1, in the first space, an object B1, which is not meant to be visible to the persons H1 and H2 in the second space (which is meant to be hidden in an invisible state), exists. On the other hand, in the second space, persons (for example, the persons H1 and H2, and the like) can freely move.

Figure 2:
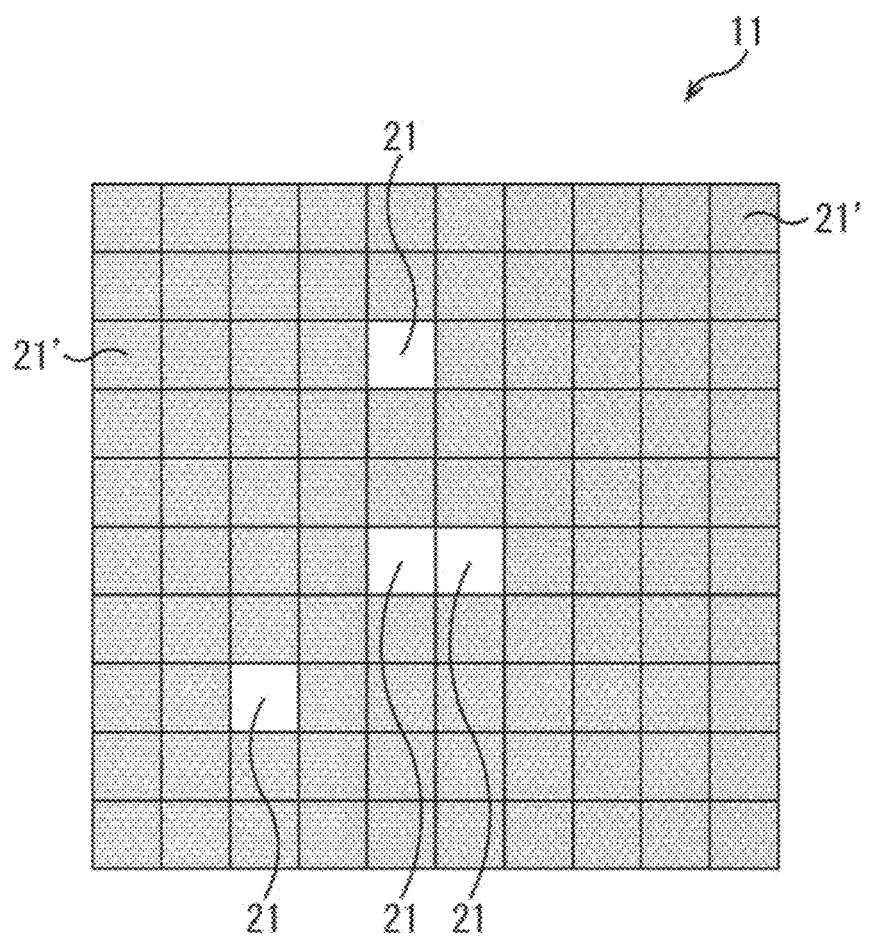
FIG. 2 is a view illustrating a light-shielding wall of the light-shielding device illustrated in FIG. 1.

For example, as illustrated in FIG. 2, the light-shielding wall 11 includes a plurality of the panels 21. For example, each of the panels 21 is a liquid crystal panels having the size of approximately 10 cm×10 cm, and are controlled to the light-shielding state or the transmitting state by the control unit 13. However, the transmitting state includes states which are controlled to various transmittances. Furthermore, the size of the panel 21 is not limited to the size of approximately 10 cm×10 cm, and may be a size smaller than the size. In addition, FIG. 2 illustrates an example in which the panel 21 has a rectangular shape, but the panel 21 may not be the rectangular shape, and may be other shapes. The panel 21 may have a polygonal shape including a triangular shape, a circular shape, or other geometric figures. In addition, the panel 21 may have a configuration other than the liquid crystal panel as long as the panel 21 can be controlled to either a light-shielding state capable of being controlled to various transmittances, or the transmitting state. Further, one sheet of the panel 21 may be divided into fine regions, and the regions may be controlled to individual transmittances. In other words, a minimum unit for controlling the light-shielding state or the transmitting state may be the panel 21 or the finely divided region. The minimum unit may be a panel unit or a region unit. However, in the embodiments of the present disclosure, description will be made on the assumption that the panel 21 is set as a control unit unless otherwise stated.

Furthermore, in FIG. 2, in a case where the panel 21 is in the light-shielding state, it is assumed that even when a person visually observes the panel 21 with naked eyes, it enters a state in which a person cannot recognize (view) an object that exists on an opposite side of the panel 21. In addition, in a case where the panel 21 is in the transmitting state, it is assumed that when the person visually observes the panel 21 with naked eyes, it enters a state in which the person can recognize (view) the object that exists on the opposite side of the panel 21. Furthermore, in FIG. 2, the panel 21 in the transmitting state is noted as "panel 21", and the panel 21 in the light-shielding state is noted as "panel 21'".

Figure 3:
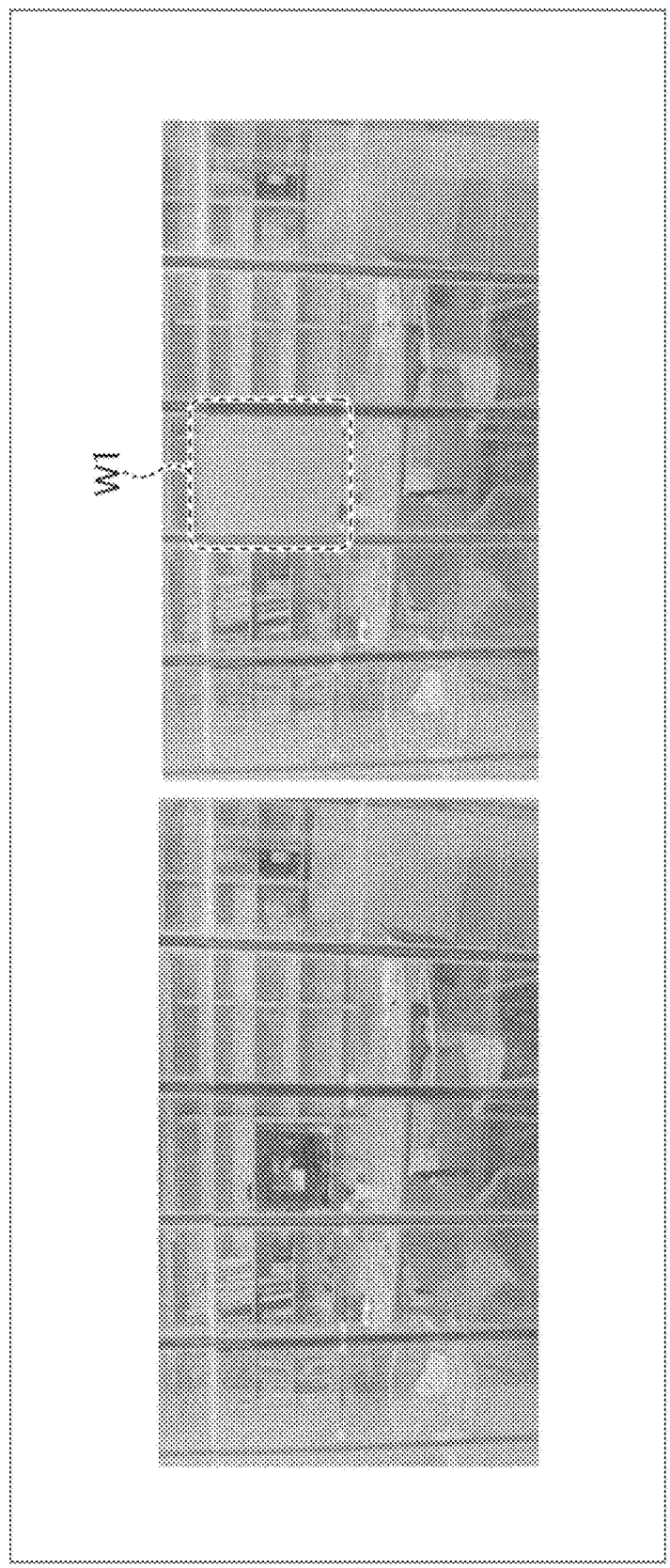
FIG. 3 is a view illustrating the light-shielding wall of the light-shielding device illustrated in FIG. 1.

More specifically, for example, in a case where the light-shielding wall 11 exists on a front side, and a conference room exists on a rear side of the light-shielding wall 11, when the panels 21 are controlled to the light-shielding state, it enters a state in which the inside of the conference room is invisible (a state in which the inside cannot be visually recognized) as illustrated by the inside of a region W1 surrounded by a dot line at a right portion in FIG. 3. In addition, as illustrated by regions other than the region W1, when the panels 21 are controlled in the transmitting state, it enters a state in which the inside of the conference room is visible (a state in which the inside can be visually confirmed).

The cameras 12-1 and 12-2 capture an image of the first space and the second space, and supply the captured image to the control unit 13. Furthermore, in the following description, in a case where it is not necessary to particularly discriminate the cameras 12-1 and 12-2, it is assumed that the cameras 12-1 and 12-2 are referred to as simply as "camera 12", and this is also true of other configurations. More specifically, the cameras 12-1 and 12-2 respectively include optical blocks 12a-1 and 12a-2, image sensors 12b-1 and 12b-2, and signal processing units 12c-1 and 12c-2. The optical block 12a includes at least one or more sheets of lenses and condenses light to focus the light to the image sensor 12b. The image sensor 12b converts the focused light that is incident through the optical block into a signal corresponding to a light quantity in a pixel unit that is disposed in an array shape, and outputs the signal to the signal processing unit 12c. The signal processing unit 12c performs predetermined signal processing with respect to signals supplied from respective pixels to generate an image constituted by pixel signals, and outputs the generated image to the control unit 13. Here, the cameras 12-1 and 12-2 respectively capture images, and capture images including distance data from the cameras 12-1 and 12-2 in a space in a subject image captured with respect to respective pixels.

That is, the cameras 12-1 and 12-2 have a camera function that is so-called depth camera. According to this, the images captured by the cameras 12-1 and 12-2 include information distances from the camera 12-1 and 12-2 to the subject in a pixel unit in addition to a typical image. Furthermore, in the following description, it is assumed that an image constituted by distance information in a pixel unit is referred to as a distance image. Accordingly, the cameras 12-1 and 12-2 capture a typical image, generate the distance image, and supply the distance image to the control unit 13.

The control unit 13 includes a control circuit such as one or a plurality of central processing units (CPU), and acquires images of the first space and the second space which are respectively supplied from the cameras 12-1 and 12-2. The control unit 13 recognizes a position of the object B1 in the first space on the basis of the image of the first space, and information of an installation position and a direction of the camera 12-1. In addition, the control unit 13 specifies eye positions E1 and E2 of the persons H1 and H2 to whom the object B1 is not meant to be visible on the basis of the image of the second space and information of an installation position and a direction of the camera 12-2. Further, the control unit 13 acquires optical paths L1 and L2 of the object B1 from the eye positions E1 and E2 of the persons H1 and H2 to whom the object B1 is not meant to be visible. The optical paths L1 and L2 may be also be referred to as paths of visual lines when visually observing the object B1 from the eye positions E1 and E2 of the persons H1 and H2 to whom the object B1 is not meant to be visible.

In addition, the control unit 13 controls panels 21 including intersections with the optical paths L1 and L2 among the panels 21 on the light-shielding wall 11 to the light-shielding state, and controls the other panels 21 to the transmitting state. According to the control, it is possible to maintain the second space as a bright and spacious space while maintaining the object B1 that exists in the first space in an invisible state with respect to the persons H1 and H2 who are in the second space. That is, for example, the transmitting state becomes a state in which a room on the other side is visible over the light-shielding wall 11 as illustrated at a left portion in FIG. 3. On the other hand, the light-shielding state is a state in which the room on the other side is invisible as indicated by the region W1 at a left portion in FIG. 3.

Furthermore, in FIG. 1, the optical paths express visual lines when the eyes E1 and E2 of the persons H1 and H2 are set as visual points, but the optical paths may represent paths of light that is transmitted through or shielded by the light-shielding wall 11. Accordingly, the optical paths may not express the visual lines, and for example, a path that represents a route of sunlight of which a light source is the sun is also called an optical path. Here, in the following description, it is assumed that routes of light, which is transmitted through the light-shielding wall 11 when the respective panels 21 of the light-shielding wall 11 is controlled to the transmitting state, are referred to as "optical path".

In addition, in a state in which a position of the object B1 in a space can be recognized in advance, the camera 12-1 is not particularly necessary, and a configuration including only the camera 12-2 may be employed. In addition, in the case of the sunlight of which a light source is the sun, the sunlight can be regarded as being approximately parallel on the earth, and an optical path can be obtained if an azimuth and a direction of the light-shielding wall 11 can be recognized. Accordingly, even in this case, a configuration including only the camera 12-2 may be employed.

Further, description has been given of an example in which a panel 21 on an optical path, on which an object meant to be invisible to a predetermined user through the light-shielding wall 11 is visible, is set to the light-shielding state, and the other panels 21 are set to the transmitting state. However, in contrast to the example, in a case where an object, which may be visible to a predetermined user through the light-shielding wall 11 but is meant to be invisible to users other than the predetermined user, exists, only a panel 21 on an optical path from the predetermined user to the object may be set to the transmitting state, and the other panels 21 may be set to the light-shielding state.

2. First Embodiment

<Example of Light-Shielding Device of Allowing User to Comfortably Wake Up>

The above-described light-shielding wall 11 can be used like window glass when the panels 21 are set to the transmitting state, and can be allowed to function as a blind when the panels 21 are set to the light-shielding state. Here, in the first embodiment of the light-shielding device to which the technology of the present disclosure is applied, description will be given of an example in which the above-described light-shielding wall 11 is used as a window.

Figure 4:
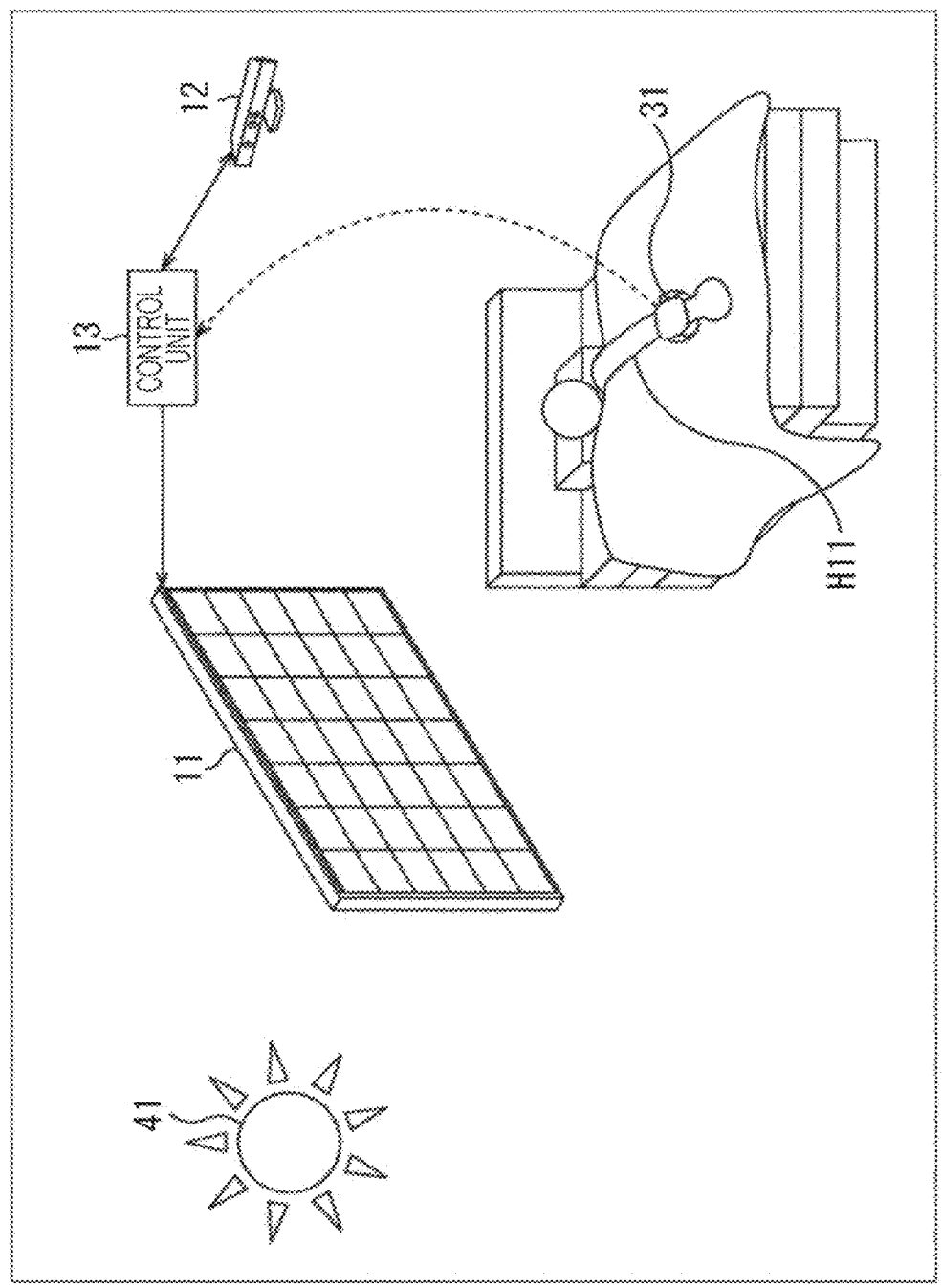
FIG. 4 is a view illustrating a configuration example of a first embodiment of the light-shielding device according to the present disclosure.

FIG. 4 illustrates a configuration example of the light-shielding device in a case where the light-shielding wall 11 is used as window glass. The light-shielding device illustrated in FIG. 4 can be used as a window by setting the respective panels 21 of the light-shielding wall 11 to the transmitting state. In addition, the light-shielding device can be allowed to function as a blind by changing a transmittance even in the light-shielding state or the transmitting state. In this case, the window constituted by the light-shielding wall 11 separates an interior that is a bed room in which a user sleeps, and an exterior that is an outer side of the window.

In addition, in the light-shielding device illustrated in FIG. 4, in a case where the light-shielding wall 11 is used, for example, as a window of a bed room and is set to the light-shielding state when going to bed, and an alarm time of an alarm is set, the light-shielding state and the transmitting state of the respective panels 21 of the light-shielding wall 11 are controlled in correspondence with an orientation of a user's face as biological information of the user, and the depth of sleep to allow the user to comfortably wake up.

That is, the light-shielding device illustrated in FIG. 4 obtains the depth of sleep on the basis of biological information for obtaining a sleep state of the user such as a pulse rate, a body temperature, a blood pressure, a breathing frequency, and a body turning frequency of the user, specifies an easily waking-up time which is near the alarm setting time and at which the depth of sleep of the user is shallow, and controls the light-shielding state or the transmitting state of the respective panels 21 of the light-shielding wall 11 at the specified time in correspondence with the biological information such as a face orientation to allow the user can visually recognize solar light when the user wakes up. According to this, the user can comfortably wake up. That is, the light-shielding device illustrated in FIG. 4 controls the light-shielding state or the transmitting state of the respective panels 21 of the light-shielding wall 11 at an easily waking-up timing on the basis of two kinds of biological information such as the depth of sleep and the face direction so that the user can visually recognize solar light when the user wakes up so as to allow the user comfortably wakes up.

Furthermore, it is said that visual recognition of the solar light when waking up has an effect of deriving waking-up by resetting a biological clock, and thus the light-shielding device illustrated in FIG. 4 allow the user to comfortably wake up by using the effect. Furthermore, in a case where a light source, which derives waking-up, exists indoors in addition to the solar light, the light source may be used instead of the solar light. For example, an illumination with a large light quantity similar to the light quantity of the solar light, and the like may be used as the light source.

More specifically, the light-shielding device illustrated in FIG. 4 includes the light-shielding wall 11 that is used as a window of a bed room, a camera 12 that captures an image of a user H11 who sleeps in the bed room, a biological sensor 31 that acquires biological information of the user H11, and the control unit 13 that controls any one of the light-shielding state, the transmitting state, and the transmittance adjusting state of the respective panels 21 of the light-shielding wall 11 on the basis of an image captured by the camera 12 and biological information supplied from the biological sensor 31.

That is, in a case where a user who sleeps in the bed room sets an alarm time as an alarm function, when the user falls asleep, the control unit 13 sets the panels 21 of the light-shielding wall 11 as a window to a dark state in which it is easy to fall asleep as the light-shielding state. In addition, for example, the control unit 13 acquires biological information including any one or a plurality of values among a body temperature, a pulse rate, a blood pressure, a breathing frequency, and body turning of the user from the biological sensor 31, and obtains an easily waking-up time which is near time set as an alarm of the alarm function and at which the depth of sleep of the user is shallow. Then, the control unit 13 obtains a face orientation of the user H11 from an image captured by the camera 12, and adjusts the light-shielding state or the transmitting state of the respective panels 21 of the light-shielding wall 11 as the window from an incident direction, an incident angle, and the like of light of which a light source is the sun 41 to allow the user to comfortably wake up at timing at which the user easily wakes up in a state of visually recognizing solar light.

<Configuration Example of Realizing Light-Shielding Device Illustrated in FIG. 4>

Next, a detailed configuration for realizing the light-shielding device illustrated in FIG. 4 will be described with reference to a block diagram in FIG. 5. Furthermore, the light-shielding wall 11 and the camera 12 which constitute the window have the same function as described with reference to FIG. 1 to FIG. 3, and thus description thereof will be appropriately omitted.

The control unit 13 includes a position information acquisition unit 62, a position information storage unit 63, a time information input unit 64, a light-shielding wall direction input unit 65, a solar light incident angle calculation unit 66, a face detection unit 67, a light-shielding and transmitting position calculation unit 68, a transmittance calculation unit 69, a light-shielding and transmitting storage unit 70, a light-shielding and transmitting control unit 71, an alarm setting unit 72, a degree-of-sleep-depth calculation unit 73, and a biological information acquisition unit 74.

The position information acquisition unit 62 acquires latitude and longitude information indicating a position of the light-shielding wall on the earth, and stores the information in the position information storage unit 63. The latitude and longitude information is supplied from a global positioning system (GPS) module 61 that receives a signal from a plurality of satellites (not illustrated) and calculates an own position on the earth as the information of latitude and longitude in accordance with the received signal. Furthermore, a current position can be acquired on the basis of a signal intensity that is received from a portable telephone base station or a wireless local area network (LAN) base station other than the GPS. In addition, acquisition processing stated here may be performed by various methods such as direct data obtainment, for example, obtainment of sensing data by a sensor and the like, reception of transmitted data, and reading-out of data recorded in a storage medium.

Examples of the position information storage unit 63 include a hard disc drive (HDD), a solid state drive (SSD), and the like. The position information storage unit 63 stores the information of latitude and longitude which is supplied from the position information acquisition unit 62, and supplies the stored information of latitude and longitude to the solar light incident angle calculation unit 66 as necessary.

The time information input unit 64 stores time information corresponding to a current time, and supplies corresponding date information to the solar light incident angle calculation unit 66 as necessary. Not only the date information, but also date and time information may be included.

The light-shielding wall direction input unit 65 reads an installation direction of the light-shielding wall 11 with respect to the control unit 13 on the basis of an image captured by the camera 12, and supplies the direction to the solar light incident angle calculation unit 66 as installation direction information of the light-shielding wall 11.

The biological information acquisition unit 74 receives biological information supplied from the biological sensor 31, and supplies the biological information to the degree-of-sleep-depth calculation unit 73. In addition, the biological information acquisition unit 74 detects, for example, body turning of the user H11 and the like from the image supplied from the camera 12 as biological information, and supplies the biological information to the degree-of-sleep-depth calculation unit 73.

For example, the biological sensor 31 is a wrist watch type sensor and is used in a state of being wound around a wrist. The biological sensor 31 detects a body temperature, a heartbeat, a blood pressure, a breathing frequency, and the like of a user as biological information, and transmits the detection result to the biological information acquisition unit 74 of the control unit 13 through radio communication such as Wifi and Bluetooth (registered trademark). Furthermore, as the biological sensor 31, the wrist watch type sensor is exemplified. However, the biological sensor 31 may be embedded in a smartphone as an application program and may be used in a state of being wound around the wrist. In addition, communication between the biological sensor 31 and the control unit may be another communication, and may be wired communication or the like. However, it is preferable that the communication does not interrupt sleep of the user. Further, the biological information may be information other than information measured by the biological sensor 31, and may be biological information such as, for example, body turning that is obtained on the basis of a captured image obtained by capturing an image of the user with the camera 12.

The alarm setting unit 72 is configured to accept and store setting information that is input from an outer side when an external operation button (not illustrated) or the like is operated by the user. The alarm setting unit 72 accepts a setting time of an alarm as an alarm function, and supplies the time information to the degree-of-sleep-depth calculation unit 73. Furthermore, as in a typical alarm, the alarm setting unit 72 may be provided with a function of outputting an alarm sound at a setting time as necessary.

The degree-of-sleep-depth calculation unit 73 estimates an easily waking-up time which is near the alarm setting time and at which the depth of sleep of the user is shallow on the basis of the biological information that is supplied form the biological information acquisition unit 74 and the information of the alarm setting time that is supplied from the alarm setting unit 72, and supplies the estimated time to the solar light incident angle calculation unit 66, the light-shielding and transmitting position calculation unit 68, and the transmittance calculation unit 69.

The solar light incident angle calculation unit 66 calculates a solar light incident angle that is a direction in which light of which a light source is the sun 41 is transmitted through the light-shielding wall 11 that is a window as time series information on the basis of the own latitude and longitude information stored in the position information storage unit 63, the time information transmitted from the time information input unit 64, and the installation direction information of the light-shielding wall 11 which is supplied from the light-shielding wall direction input unit 65, and supplies the information to the light-shielding and transmitting position calculation unit 68 and the transmittance calculation unit 69.

The face detection unit 67 detects a face image of the user from an image captured by the camera 12, and supplies spatial position information of the user's face with respect to the light-shielding wall 11, which is obtained from in-image position information of the face image, to the light-shielding and transmitting position calculation unit 68.

The light-shielding and transmitting position calculation unit 68 obtains an optical path in which the user's face is irradiated with light of which a light source is the sun 41 on the basis of solar light incident angle information supplied from the solar light incident angle calculation unit 66, position information of the user's face supplied from the face detection unit 67, and information of the easily waking-up time, which is near the alarm setting time and at which the depth of sleep is shallow, transmitted from the degree-of-sleep-depth calculation unit 73, calculates a position of a panel 21 on the light-shielding wall 11 on the obtained optical path, and stores the position in the light-shielding and transmitting storage unit 70 as light-shielding and transmitting information.

That is, it is assumed that when user's eyes are irradiated with solar light at a waking-up timing, waking-up can be encouraged even in a state in which the eyes are closed. Here, the light-shielding and transmitting position calculation unit 68 obtains the optical path in which the user's eyes are irradiated with light and sets the panel 21 on the optical path to the transmitting state to irradiate the user's eyes with the light of which a light source is the sun 41 at the time which is near the alarm setting time as an alarm function and at which the user easily wakes up.

The transmittance calculation unit 69 calculates a transmittance of the panel 21 that is set to the transmitting state in the light-shielding wall 11 on the basis of the solar light incident angle information supplied from the solar light incident angle calculation unit 66, and the information of the easily waking-up time which is transmitted from the degree-of-sleep-depth calculation unit 73 and is near the alarm setting time and in which the depth of sleep is shallow, and stores the transmittance in the light-shielding and transmitting storage unit 70 as light-shielding and transmitting information.

That is, when encouraging waking-up by irradiating the user's eyes with light of which a light source is the sun 41, the transmittance is set to realize an appropriate light quantity so that the light quantity does not become an extremely high light quantity, or an extremely low light quantity with which waking-up cannot be encouraged in correspondence with an incident direction of the solar light.

The light-shielding and transmitting information is information in which the respective panels 21 are set and registered to either the light-shielding state or the transmitting state, and a transmittance in the transmitting state is set and registered. Accordingly, in the light-shielding and transmitting information, with regard to setting of the respective panel 21 to either the light-shielding state or the transmitting state, the setting is performed by the light-shielding and transmitting position calculation unit 68, and the transmittance of a panel 21 set to the transmitting state is set by the transmittance calculation unit 69. In addition, each of the panels 21 may be divided into fine regions, and the regions may be controlled to either the light-shielding state or the transmitting state. In this case, the light-shielding and transmitting information becomes information indicating that the regions will be set to which state between the light-shielding state and the transmitting state. In addition, the information registered as the light-shielding and transmitting information may be information indicating a transmittance or a light-shielding rate which corresponds to information indicating that setting will be made to which state between the light-shielding state and the transmitting state. For example, the transmittance may be set as "1−light-shielding rate".

Furthermore, the user's face may not be directly irradiated with light of which a light source is the sun 41 through the light-shielding wall 11 in accordance with the solar light incident angle. In this case, the entirety of the panels 21 of the light-shielding wall 11 may be set to the transmitting state to take light as environmental light into the entirety of a room so as to irradiate the user's eyes with the light.

The light-shielding and transmitting control unit 71 controls the light-shielding state and the transmitting state that considers the transmittance in the panels 21 of the light-shielding wall 11 in correspondence with the light-shielding and transmitting information which is stored in the light-shielding and transmitting storage unit 70 and in which information of the transmitting state or the light-shielding state of the respective panels 21 in the light-shielding wall 11, and information of each transmittance of transmitting panels 21 are registered.

Figure 5:
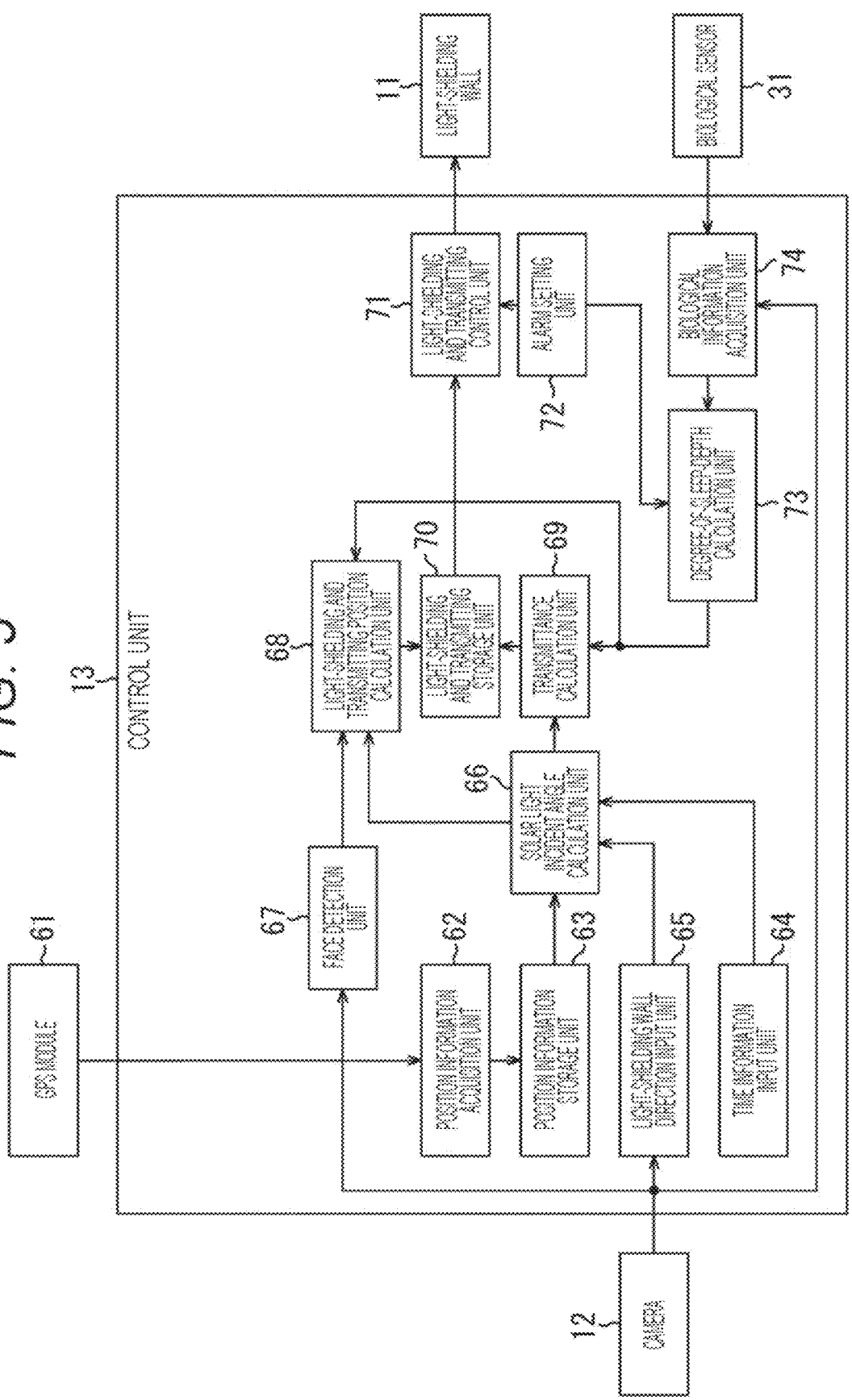
FIG. 5 is a block diagram illustrating a function of realizing the light-shielding device illustrated in FIG. 4.

<Comfortable Waking-Up Control Processing by Light-Shielding Device Illustrated in FIG. 5>

Figure 6:
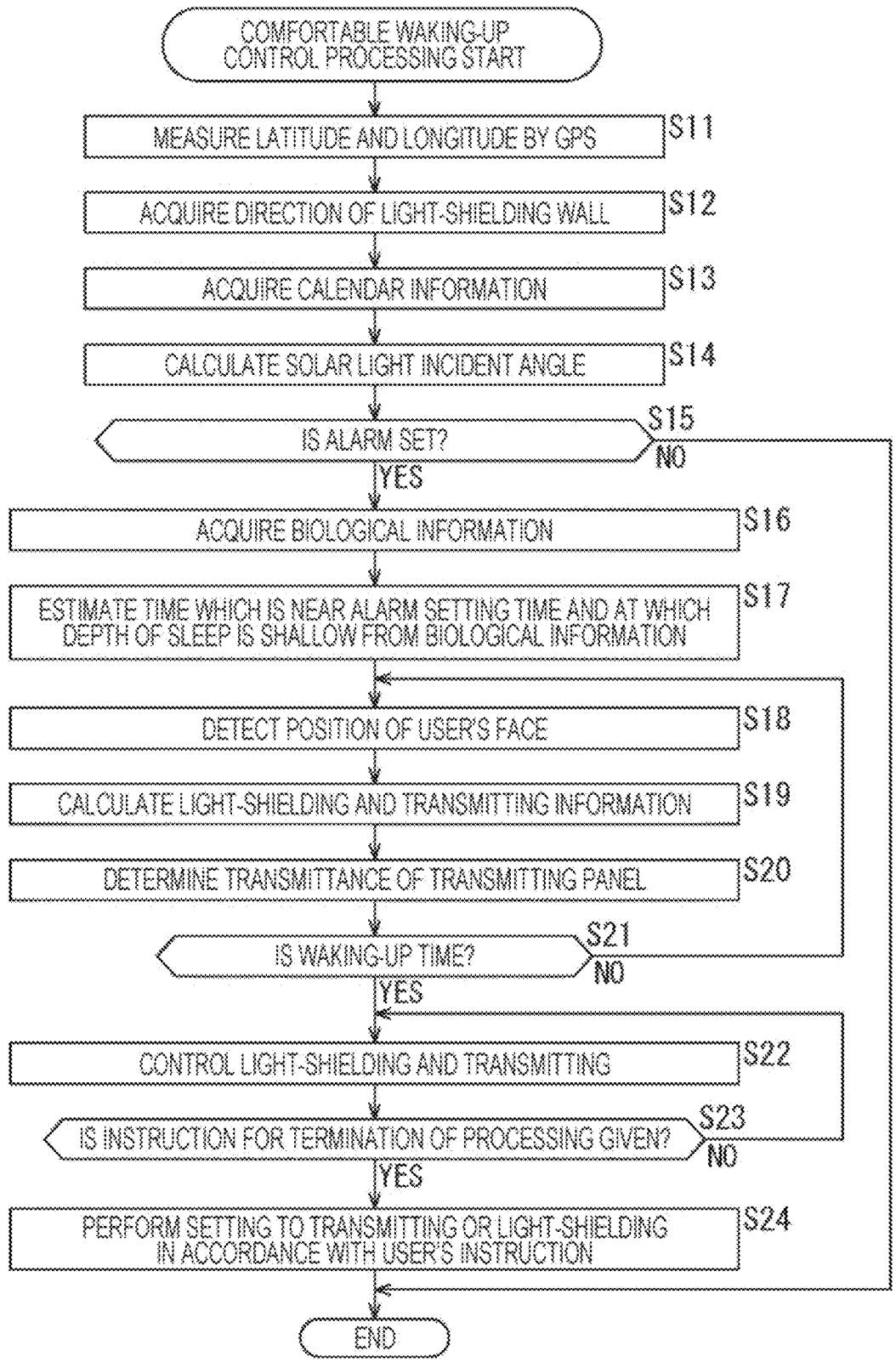
FIG. 6 is a flowchart illustrating comfortable waking-up control processing by the light-shielding device illustrated in FIG. 5.

Next, description will be given of comfortable waking-up control processing in the control unit 13 of the light-shielding device illustrated in FIG. 5 with reference to a flowchart in FIG. 6.

In step S11, the position information acquisition unit 62 controls the GPS module 61 to measure latitude and longitude information that is own information on the earth on the basis of a signal transmitted by electric waves from a satellite (not illustrated), and acquires the measurement result and stores the measurement result in the position information storage unit 63.

In step S12, on the basis of an image captured by the camera 12, the light-shielding wall direction input unit 65 obtains an installation direction of the light-shielding wall 11 in an actual space from a position of an image of the light-shielding wall 11 in the captured image, and supplies the installation direction to the solar light incident angle calculation unit 66 as a light-shielding wall direction.

In step S13, the time information input unit 64 supplies information of a current date for specifying an orbit of the sun from the time information that is stored to the solar light incident angle calculation unit 66.

In step S14, the solar light incident angle calculation unit 66 reads out latitude and longitude information which is stored in the position information storage unit 63 and indicates a own position on the earth, calculates a solar light incident angle, which is an angle of an incident direction of light of which a light source is the sun 41 with respect to the light-shielding wall 11, form the time information transmitted from the time information input unit 64 and the installation direction of the light-shielding wall 11, and supplies the solar light incident angle to the light-shielding and transmitting position calculation unit 68 and the transmittance calculation unit 69. At this time, the solar light incident angle information is supplied to the light-shielding and transmitting position calculation unit 68 and the transmittance calculation unit 69 as time series information.

In step S15, the alarm setting unit 72 determines whether or not an alarm time of an alarm is set in a current state. In step S15, in a case where it is determined that the alarm time of the alarm is not set, the processing is terminated.

In addition, in step S15, in a case where it is determined that the alarm time of the alarm is set, the processing proceeds to step S16.

In step S16, the biological information acquisition unit 74 makes a request for the biological sensor 31 to transmit biological information, acquires the biological information transmitted in response to the request, and supplies the biological information to the degree-of-sleep-depth calculation unit 73.

Furthermore, it may be assumed that the biological information is always supplied from the biological sensor 31, and the biological information acquisition unit 74 stores the biological information in time series, and uses the time series biological information that is stored as necessary. In addition, the biological information acquisition unit 74 may always acquire body turning information from an image captured by the camera 12 as the biological information, may store the information in time series, and may read out the information for use as necessary.

In step S17, the degree-of-sleep-depth calculation unit 73 obtains time series depth of sleep on the basis of the biological information that is supplied and an alarm time that is set by the alarm setting unit 72, and calculates an easily waking-up time which is near the alarm setting time and at which the depth of sleep is shallow. In the following description, the time at which the user easily wakes up is referred to as a waking-up time.

In step S18, the face detection unit 67 detects a face image of the user H11 from an image captured by the camera 12, calculates a position of a face from an in-image position of the detected face image by using a positional relationship between the light-shielding wall 11 and the face of the user H11 in an actual space, and supplies the position to the light-shielding and transmitting position calculation unit 68.

In step S19, the light-shielding and transmitting position calculation unit 68 determines that the respective panels 21 of the light-shielding wall 11 is set to which state between the light-shielding state and the transmitting state on the basis of the solar light incident angle information, the position information of the user's face, and the information of the waking-up time at which the user easily wakes up so that the user can be irradiated with light of which a light source is the sun 41 so as to encourage the user to comfortably wake up at time set as a waking-up time, and stores the determined state in the light-shielding and transmitting storage unit 70 as light-shielding and transmitting information.

In step S20, the transmittance calculation unit 69 sets a transmittance of a transmitting panel on the basis of the solar light incident angle information and information of time set as the waking-up time on the basis of the information of the waking-up time at which the user easily wakes up, and stores the transmittance in the light-shielding and transmitting storage unit 70 as light-shielding and transmitting information.

In step S21, the light-shielding and transmitting control unit 71 determines whether or not the current time is the waking-up time on the basis of the alarm time that is set by the alarm setting unit 72. For example, in a case where it is determined that the current time is not the waking-up time, the processing returns to step S18, and the processing from steps S18 to S21 is repeated until it reaches the waking-up time. That is, even when the user performs body turning and the like before reaching the waking-up time, setting of the light-shielding and transmitting information for allowing the user's eyes to enter a state of being appropriately irradiated with the solar light when reaching the waking-up time is altered and continued.

Then, in step S21, when reaching the waking-up time, the processing proceeds to step S22.

In step S22, the light-shielding and transmitting control unit 71 controls the light-shielding and transmitting information stored in the light-shielding and transmitting storage unit 70, that is, the respective panels 21 in the light-shielding wall 11 to either the light-shielding state or the transmitting state, and controls light-shielding and transmitting of the respective panels 21 so that a panel 21 in the transmitting state enters a state based on the transmittance information.

In step S23, the light-shielding and transmitting control unit 71 determines whether or not an instruction for termination of processing is given. In a case where it is determined that the instruction for termination of processing is not given, the processing returns to step S22, and light-shielding or transmitting of the respective panels 21 in the light-shielding wall 11 is controlled.

Then, in step S23, in a case it is determined the instruction for termination of processing is given, the processing proceeds to step S24.

In step S24, the light-shielding and transmitting control unit 71 controls the light-shielding and transmitting of the respective panels 21 of the light-shielding wall 11 so that the panels 21 enter either the light-shielding state or the transmitting state which is set for each panel 21 of the light-shielding wall 11 by the user in advance.

Through the above-described processing, an easily waking-up time, which is near the time set as an alarm and at which the depth of sleep is shallow, is set as the waking-up time on the basis of the biological information, and the transmitting state or the light-shielding state of the respective panels 21 of the light-shielding wall 11 that functions as a window is controlled so that the user's eyes can be irradiated with light of which a light source is the sun 41 in order for the user to wake up at the waking-up time. Accordingly, it is possible to encourage the user to comfortably wake up. Furthermore, the user has waked up already at time near the alarm time in some cases, the processing from step S17 to step S21 may be performed as follows. That is, it reaches a time near the alarm time at which a remaining time up to the alarm time is within a predetermined time, the degree-of-sleep-depth calculation unit 73 determines whether or not the user H11 is sleeping, that is, the user is in a sleep state in the current time on the basis of the biological information that is supplied up to now. Then, in a case of a state in which the user has waked up already at the time near the alarm time instead of the sleep state, the degree-of-sleep-depth calculation unit 73 sets the current time as the waking-up time. That is, in a case of a state in which the user has waked up already at the time near the alarm time, it is considered that the user has spontaneously waked up at the time near the alarm time, and the current time is set as the waking-up time. In addition, at time near the alarm time at which a remaining time up to the alarm time is within a predetermined time, in a case where determination is made as the sleep state, and the user does not wake up, the degree-of-sleep-depth calculation unit 73 estimates the depth of sleep as a time series variation up to the alarm time on the basis of the biological information that is supplied up to now. Then, the degree-of-sleep-depth calculation unit 73 sets a time, which is estimated as the shallowest sleep time in a period from the current time to the alarm time, as the waking-up time. That is, it can be said that the biological information is information for obtaining the depth of sleep, and information for determining whether or not the user is in the sleep state.

In addition, an alarm sound of a typically used alarm may be emitted simultaneously with the above-described processing.

In addition, with regard to a panel 21 that is set to the transmitting state, a transmittance may be allowed to vary to be gradually raised from the waking-up time at which the user easily wakes up while avoiding rapid bright variation. In addition, in this case, it is possible to encourage comfortable waking-up.

Description has been given of an example in which the light-shielding and transmitting state of the respective panels 21 of the light-shielding wall 11 is controlled at the waking-up time in correspondence with two kinds of information including the easily waking-up time obtained on the basis of the biological information and the orientation of the user's face, but a constant effect can be obtained even when using only any one piece of information between the information of the easily waking-up time obtained on the basis of the biological information and the orientation of the user's face. However, in a case of using only the orientation of the user's face as the biological information, the waking-up time becomes the alarm setting time.

Further, description has been given of an example set to a state in which the user's eyes are irradiated with solar light at timing at which the user wakes up in order for the user to comfortably wake up, but the user may be encouraged to comfortably wake up with another direction by controlling the light-shielding state and the transmitting state of the panels 21 of the light-shielding wall 11, and by controlling the transmittance of a panel 21 in the transmitting state. For example, the light-shielding state and the transmitting state of the panel 21 of the light-shielding wall 11 may be controlled, and the transmittance of a panel 21 in the transmitting state may be controlled to be variable in accordance with a predetermined time series to realize direction in which the user's eyes are irradiated with light such as sunbeams shining through branches of trees in order for the user comfortably wakes up.

3. Second Embodiment

Description has been given of the light-shielding device in which the light-shielding wall 11 is applied as a window of a bed room, and which obtains the easily waking-up time on the basis of the biological information, and controls the light-shielding state or the transmitting state of the respective panels 21 of the light-shielding wall 11 to irradiate the user's eye with light of which a light source is the sun 41 at the obtained easily waking-up time in correspondence with the orientation of the user's face, thereby encouraging the user to comfortably wake up. However, when waking-up is detected, information necessary for daily life may be presented by controlling the light-shielding state or the transmitting state of the respective panels 21 of the light-shielding wall 11.

Figure 7:
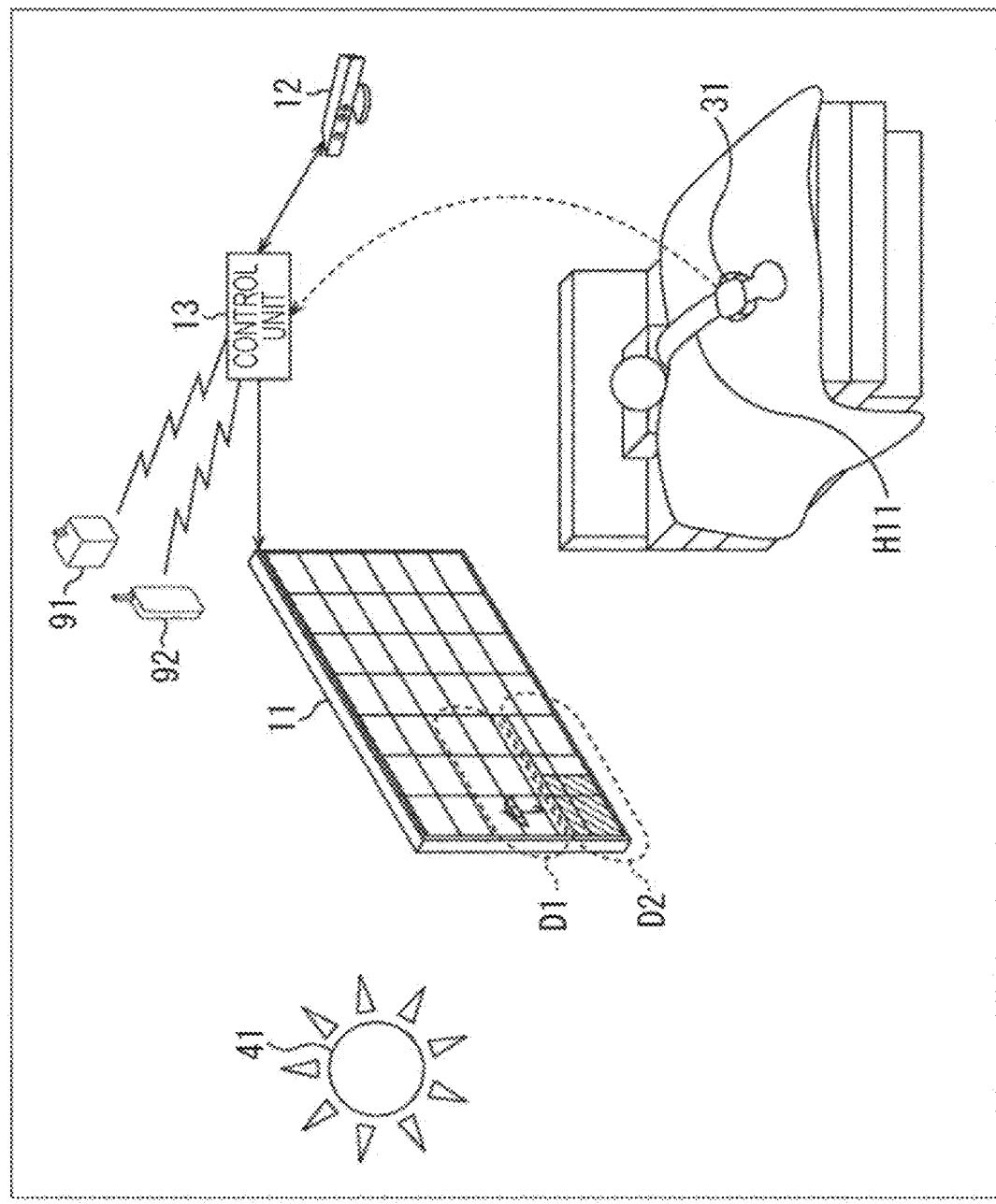
FIG. 7 is a view illustrating a configuration example of a second embodiment of the light-shielding device according to the present disclosure.

That is, for example, as illustrated in FIG. 7, a rainfall sensor 91 and a particulate matter (PM) 2.5 measuring device 92 are provided outdoors, and the rainfall sensor 91 and the PM 2.5 measuring device 92 which are provided outdoors provide respective measurement results to the control unit 13.

Then, when detecting waking-up of the user during the comfortable waking-up control processing performed to encourage the user to comfortably wake up through the series of processing, a measurement result mark D1 of the rainfall sensor 91 which includes an umbrella mark, and a measurement result mark D2 of the PM 2.5 measuring device 92 which indicates a detection amount in correspondence with an area of a light-shielding region may be presented by the light-shielding state and the transmitting state of the respective panels 21 at a position that is in a visual line direction of the user and is not in the backlight, a position in which a column and the like are not present and which can be sufficiently visually recognized, or a position such as a peripheral portion of the light-shielding wall 11 which is easy to visually recognize and does not interrupt a visual field. Furthermore, here, as the information that is presented when the user wakes up, the amount of rainfall that is detected by the rainfall sensor 91 and the PM 2.5 measuring device 92, or a detection amount of PM 2.5 are exemplified, but another information may be employed as long as the information is external information. Here, the external information is information indicating an outdoor environment, and examples thereof include "air temperature", "air pressure", "humidity", "wind speed", and "ultra violet (UV) intensity", and the like. The external information can be detected, for example, by installing an air-temperature sensor, an air-pressure sensor, a humidity sensor, a wind speed sensor, an UV intensity sensor, and the like.

However, in a case of realizing an example as illustrated in FIG. 7, it is assumed that the size of the panels 21 which constitute the light-shielding wall 11 that functions as the window is set to a size capable of realizing resolution to a certain extent capable of expressing the detection amount of PM 2.5 in correspondence with the umbrella mark or the area of the light-shielding region.

Furthermore, in the example, it cannot be said that the light-shielding state or the transmitting state of the respective panels 21 is controlled in a state without a condition in which an object that is meant to be invisible to a user exists on a rear side of the light-shielding wall 11 or a condition in which an object that is meant to be visible to the user exists on the rear side. However, as a whole, the respective panels 21 are controlled to a state (light-shielding state) in which a predetermined region on the rear side of the light-shielding wall 11 is invisible in the shape of the umbrella mark or a state (transmitting state) in which the predetermined region is visible, and thus the umbrella mark that is meant to be visible is projected onto the light-shielding wall 11, and is visually recognized. Accordingly, even in this case, it can be considered that an object meant to be visible is made to enter a state in which the object is likely to be visible by controlling the respective panels 21 of the light-shielding wall 11 to the light-shielding state or the transmitting state. In addition, with regard to an object that is meant to be invisible, if the light-shielding state or the transmitting state of the respective panels 21 is not controlled in a state of resembling a specific shape, the object is not projected onto the light-shielding wall 11. According to this, it can be considered that an object that is meant to be invisible is made to enter a state in which the object is hidden or is less likely to be visible.

<Configuration Example for Realizing Light-Shielding Device Illustrated in FIG. 7>

Next, a configuration example for realizing the light-shielding device illustrated in FIG. 7 will be described with reference to a block diagram in FIG. 8. Furthermore, in the configuration in FIG. 8, the same reference numeral and the same terminology will be given to a configuration having the same function as that of the configuration in FIG. 5, and description thereof will be appropriately omitted.

Figure 8:
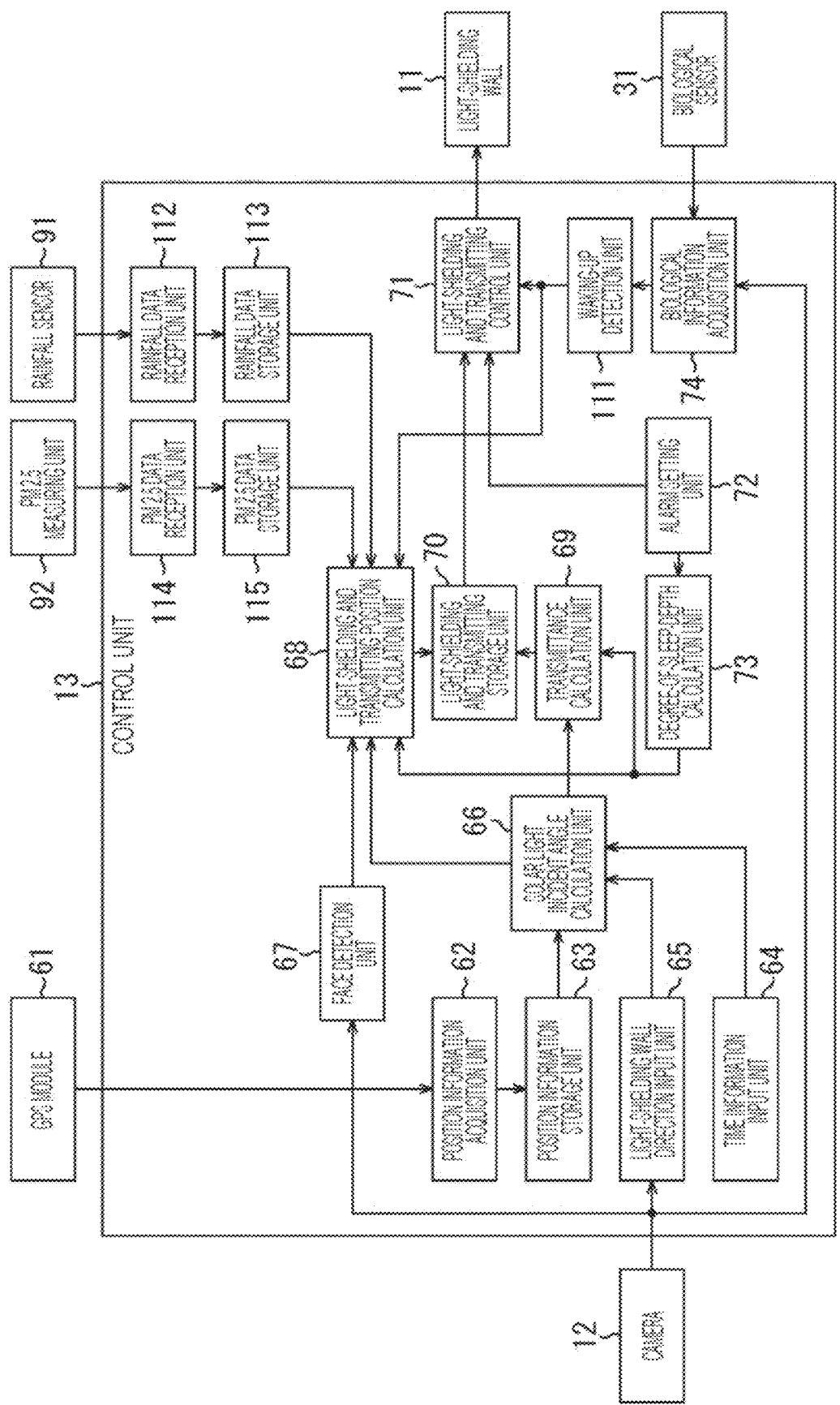
FIG. 8 is a block diagram illustrating a function of realizing the light-shielding device illustrated in FIG. 7.

Specifically, a control unit 13 in FIG. 8 is different from the control unit 13 in FIG. 5 in that a waking-up detection unit 111, a rainfall data reception unit 112, a rainfall data storage unit 113, a PM 2.5 data reception unit 114, and a PM 2.5 data storage unit 115 are further provided.

The waking-up detection unit 111 acquires biological information such as a body temperature, a heartbeat, a blood pressure, a breathing frequency, and body turning which are supplied from the biological information acquisition unit 74, detects whether or not a user wakes up after passage of an alarm time on the basis of the biological information, and supplies the detection result to the light-shielding and transmitting position calculation unit 68, and the light-shielding and transmitting control unit 71.

The rainfall data reception unit 112 receives rainfall data that is a measurement result of the rainfall sensor 91, and stores the rainfall data in the rainfall data storage unit 113.

The PM 2.5 data reception unit 114 stores PM 2.5 data that is a measurement result of the PM 2.5 measuring device 92 in the PM 2.5 data storage unit 115.

According to the processing, when receiving information indicating that a user wakes up from the waking-up detection unit 111, the light-shielding and transmitting position calculation unit 68 reads out rainfall data and PM 2.5 data which are stored in the rainfall data storage unit 113 and the PM 2.5 data storage unit 115, sets the light-shielding state or the transmitting state to control the panels 21 to display the measurement result marks D1 and D2 as illustrated in FIG. 7 in at a position that can be visually recognized in a visual line direction on the basis of position information of a user's face, and stores the state in the light-shielding and transmitting storage unit 70. Furthermore, for example, the position that can be visually recognized in the visual line direction on the basis of the position information of the user's face stated here is a position which is not in the backlight, in which a column, an obstacle, and the like are not present, and which is likely to be visually recognized. For example, the marks are displayed at a portion, which is relatively small in comparison to the entire surface of the light-shielding wall, along an end of the light-shielding wall.

When receiving the information indicating that the user wakes up from the waking-up detection unit 111, the light-shielding and transmitting control unit 71 controls the panels 21 of the light-shielding wall 11 as the window on the basis of information for controlling the panels 21 to display the measurement result marks D1 and D2 stored in the light-shielding and transmitting storage unit 70 at the position that can be visually recognized at the visual line direction on the basis of the position information of the user's face.

<Comfortable Waking-Up Processing by Light-Shielding Device Illustrated in FIG. 8>

Figure 9:
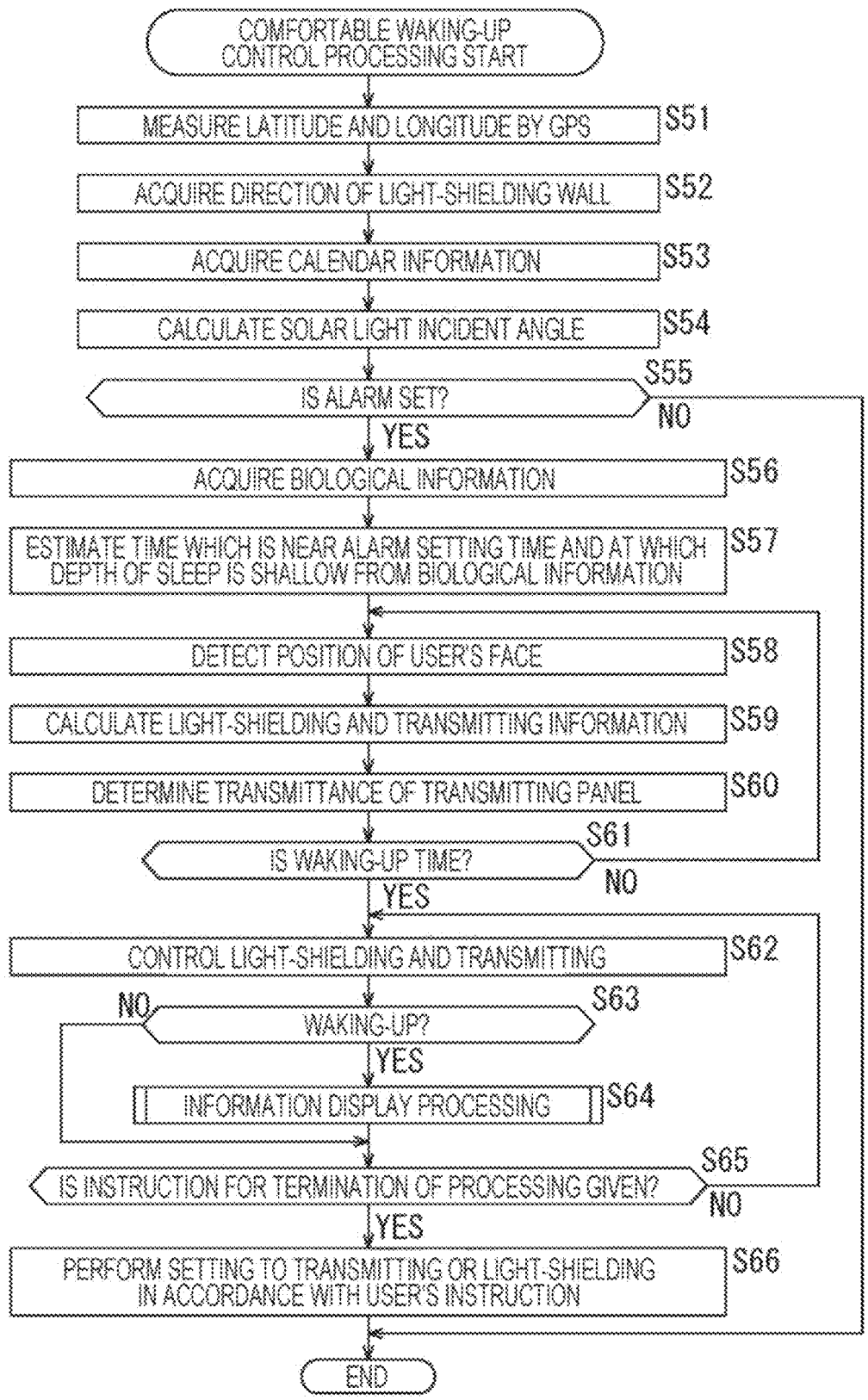
FIG. 9 is a flowchart illustrating comfortable waking-up control processing by the light-shielding device illustrated in FIG. 7.

Next, comfortable waking-up control processing in the control unit 13 of the light-shielding device illustrated in FIG. 8 will be described with reference to a flowchart in FIG. 9. Furthermore, in the flowchart in FIG. 9, processing in steps S51 to S62, S65, and S66 is processing similar to the processing in steps S11 to S24 in the flowchart in FIG. 6, and thus description thereof will be omitted.

Specifically, in step S62, it reaches the waking-up time, and the light-shielding and transmitting control unit 71 controls the light-shielding state or the transmitting state of the panels 21 of the light-shielding wall 11 as the window to encourage waking-up on the basis of the light-shielding and transmitting information stored in the light-shielding and transmitting storage unit 70, and then the processing proceeds to step S63.

In step S63, the waking-up detection unit 111 determines whether or not the user wakes up on the basis of the biological information supplied from the biological information acquisition unit 74, and in a case where it is determined that the user wakes up, the processing proceeds to step S64.

In step S64, information display processing is executed, and thus the panels 21 of the light-shielding wall 11 are controlled, and the measurement result marks D1 and D2 in FIG. 7 are displayed. Furthermore, in step S63, in a case where it is determined that the user does not wake up, the processing in step S64 is skipped.

<Information Display Processing>

Figure 10:
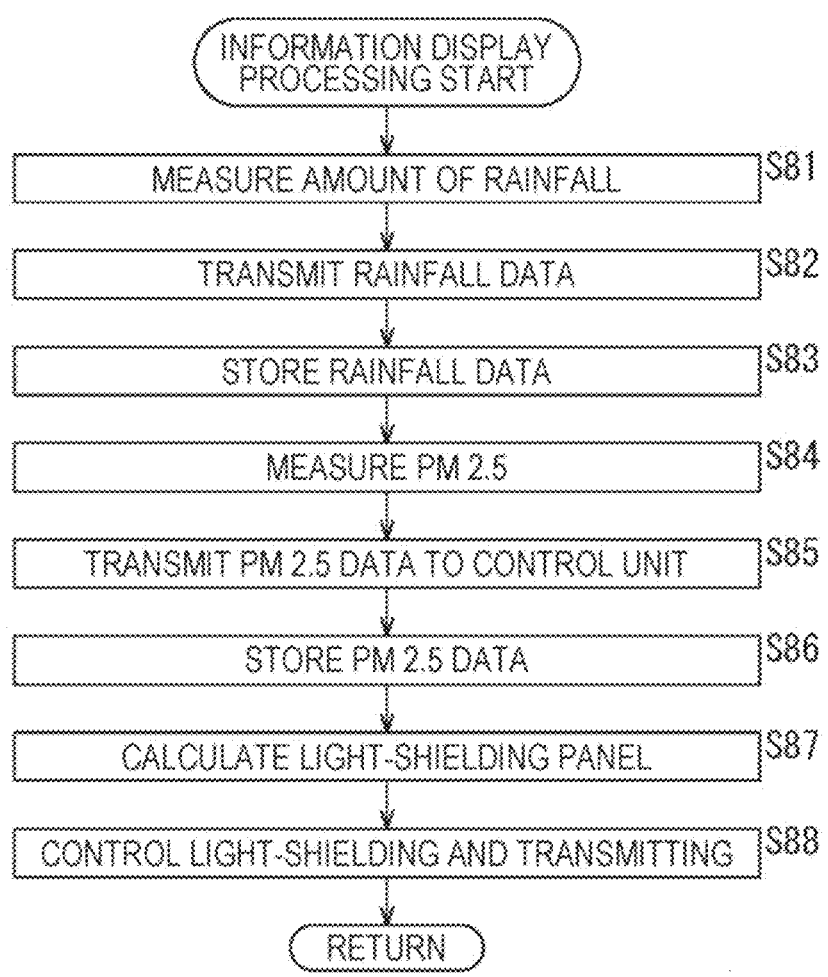
FIG. 10 is a flowchart illustrating information display processing by the light-shielding device illustrated in FIG. 7.

Here, information display processing in the control unit 13 of the light-shielding device illustrated in FIG. 8 will be described with reference to a flowchart in FIG. 10.

In step S81, the rainfall sensor 91 measures the amount of rainfall.

In step S82, the rainfall sensor 91 supplies a measurement result to the data reception unit 112 as rainfall data.

In step S83, the rainfall data reception unit 112 receives the rainfall data, and stores the rainfall data in the rainfall data storage unit 113.

In step S84, the PM 2.5 measuring device 92 measures PM 2.5.

In step S85, the PM 2.5 measuring device 92 supplies a measurement result to the PM 2.5 data reception unit 114 as PM 2.5 data.

In step S86, the PM 2.5 data reception unit 114 receives the PM 2.5 data, and stores the PM 2.5 data in the PM 2.5 data storage unit 115.

In step S87, the light-shielding and transmitting position calculation unit 68 reads out the rainfall data and the PM 2.5 data which are stored in the rainfall data storage unit 113 and the PM 2.5 data storage unit 115, generates information for every position of the panels 21 for controlling the light-shielding or transmitting of the panels 21 of the light-shielding wall 11 so as to present information of the rainfall data and the PM 2.5 data as the measurement result marks D1 and D2, and stores the information for every position in the light-shielding and transmitting storage unit 70.

In step S88, the light-shielding and transmitting control unit 71 controls the respective panels 21 of the light-shielding wall 11 to the light-shielding state or the transmitting state on the basis of the light-shielding and transmitting information stored in the light-shielding and transmitting storage unit 70.

According to the above-described processing, it is possible to display the measurement result marks D1 and D2 which are pieces of information of the rainfall data and the PM 2.5 data by the light-shielding state or the transmitting state of the respective panels 21 at a position that can be visually recognized by the user in the light-shielding wall 11 at timing at which waking-up is detected by the biological information. Furthermore, with regard to a range in which the measurement result marks D1 and D2 in FIG. 7 are displayed, the range is set to a finely divided region so that a light-shielding state or transmitting state that is finer than a peripheral panel 21 can be controlled, and thus high-resolution display can be performed in comparison to the periphery. In addition, all of the panels 21 of the light-shielding wall 11 may have a configuration that is divided into fine regions so that the light-shielding state or the transmitting state can be controlled in a finer manner.

As a result, when waking-up, it is possible to recognize a rainfall state, or the detection amount of the PM 2.5 in the outside air, and thus it is possible to determine selection of clothes, whether or not a mask is necessary, and the action of going-out early in consideration of a traffic jam due to rainfall.

Furthermore, the waking-up detection unit 111 detects whether or not the user wakes up after passage of the alarm time. In contrast, the degree-of-sleep-depth calculation unit 73 detects that a user is in a sleep state at a time near the alarm time at which a remaining time up to the alarm time is within a predetermined time on the basis of the biological information. That is, the degree-of-sleep-depth calculation unit 73 detects the sleep state at timing previous to the alarm time that is set by a user. In contrast, the waking-up detection unit 111 detects waking-up after passage of the alarm time. However, whether or not the user is in the sleep state, that is, whether or not the user wakes up is detected by any configuration. Accordingly, for example, the degree-of-sleep-depth calculation unit 73 may also function as the waking-up detection unit 111. In addition, description has been given of an example in which the presented information is the rainfall data and the PM 2.5 data, but another piece of information may be employed as long as the information can be expressed by the light-shielding wall 11. For example, the presented information may be a stock price chart that is available through the Internet and the like, and external environment information such as outside air temperature and a weather forecast.

In addition, in the description, the processing of acquiring and storing the rainfall data and the PM 2.5 data in steps S81 to S86 may be repetitively performed at all times to store the two pieces of data independently from the above-described processing flow, or the information stored by the processing in steps S87 and S88 may be read out when waking-up is detected.

Further, with regard to the measurement result marks D1 and D2, the size of the umbrella mark may be changed in accordance with the amount of rainfall, or the size of the light-shielding region may be changed in correspondence with the measurement amount of PM 2.5 to allow a quantitative value to be recognized at a time.

In addition, description has been given of an example in which the measurement result marks D1 and D2 are displayed at a position which is likely to be visually recognized by the user at a timing at which waking-up is detected. However, for example, in a case where sunshine is strong, the umbrella mark and the like are constructed by a light-shielding panel 21, and an umbrella mark that is transmitted through the light-shielding wall 11 as the window and is photographed as a shadow on the floor and the like may be displayed as information which the user visually recognize. Further, as the external information indicating an outdoor environment that is presented when waking-up is detected, "air temperature", "air pressure", "humidity", "wind speed", and "UV intensity" may be employed in addition to the amount of rainfall or the detection amount of PM 2.5. That is, for example, when information of the "wind speed" and "UV intensity" is presented as the external information, the user can determine whether or not to wear a hat today, or whether or not to wear a long sleeve shirt when the user wakes up. In addition, when information of the "air temperature", "humidity", and "wind speed" is presented as the external information, the user can determine whether or not to do the laundry. Furthermore, in this case, information of a laundry index may be presented as the external information. In addition, when information of "air pressure" is presented as the external information, it is possible to predict a future weather forecast. Alternatively, weather may be predicted and presented on the basis of the air pressure that is detected as the external information.

4. Third Embodiment

Description has been given of an example in which information is presented on the light-shielding wall 11 in a visual line direction at timing at which waking-up can be detected in correspondence with the biological information. However, for example, with regard to a case where a value indicating abnormality is shown in the rainfall data or the PM 2.5 data, it may be determined that emergency occurs, and the value may be presented regardless of a biological state.

Figure 11:
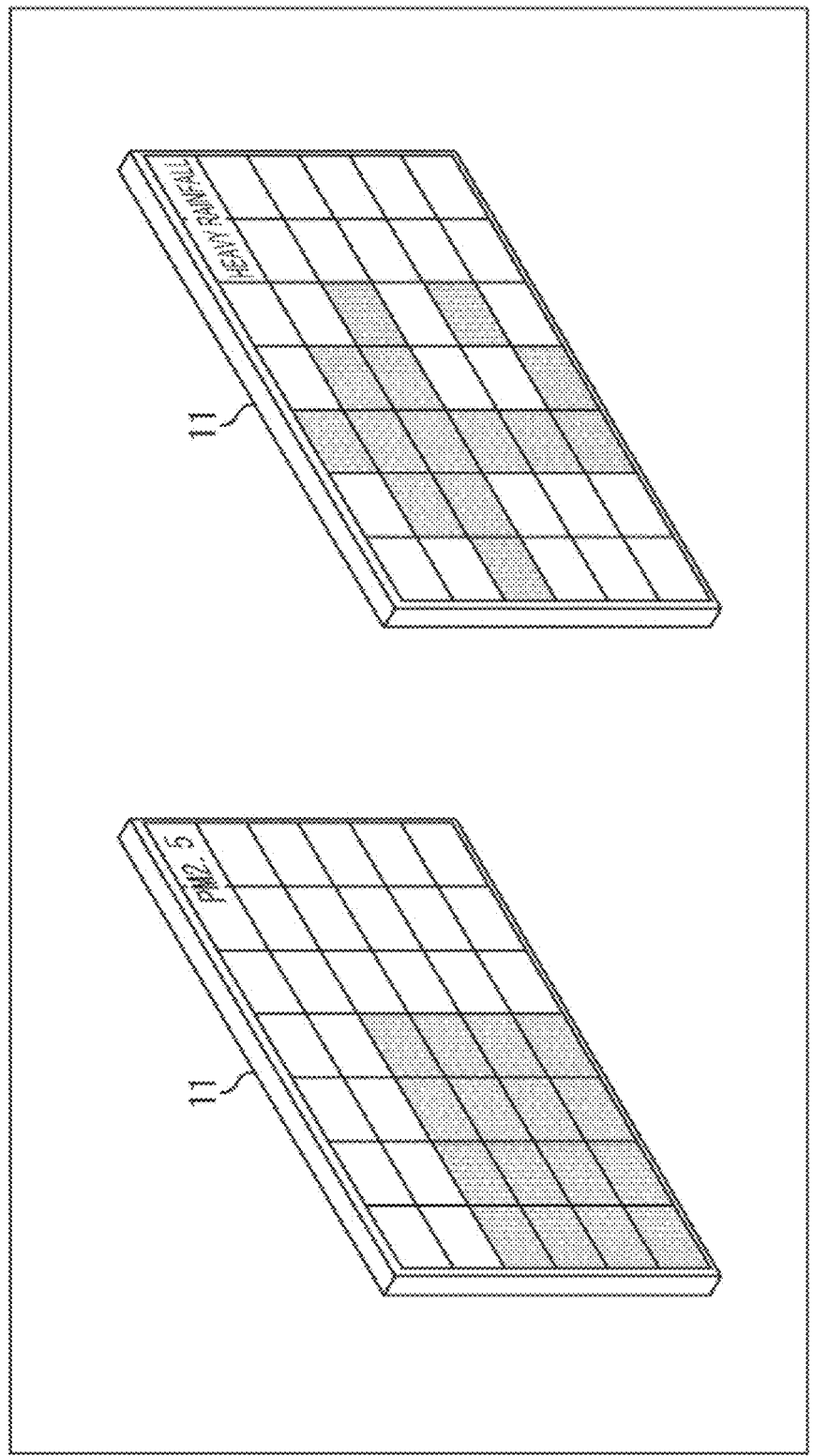
FIG. 11 is a view illustrating a configuration example of a third embodiment of the light-shielding device according to the present disclosure.

That is, in a case where the rainfall data that is a measurement result of the rainfall sensor 91 indicates heavy rainfall exceeding a predetermined reference value, for example, as illustrated at the right portion in FIG. 11, the umbrella mark is displayed at the entirety of the light-shielding wall 11 as the window or at a position such as the center that is conspicuous and is likely to be visually recognized to indicate that outdoor is heavy rainfall. In addition, in a case where the PM 2.5 data that is a measurement result of the PM 2.5 measuring device 92 exceeds the predetermined reference value, for example, as illustrated at the left portion of FIG. 11, the measurement amount of PM 2.5 is displayed as an area of a light-shielding region at the entirety of the light-shielding wall 11 as the window or at a position such as the center that is conspicuous and is likely to be visually recognized to indicate that PM 2.5 in the outside air is abnormally rich. Here, in a case where the external information does not indicate abnormality, as illustrated in FIG. 7, a mark displayed at a small site in comparison to the entire surface of the light-shielding wall 11. However, when the external information indicates abnormality, the mark may be greater than at least in comparison to display in a case where abnormality is not indicated, and a display position may be set to a location that conspicuously deviates to the center, and the like to be more likely to be visually recognized in comparison to typical display.

<Configuration Example of Realizing Light-Shielding Device Illustrated in FIG. 11>

Next, a configuration example for realizing the light-shielding device illustrated in FIG. 11 will be described with reference to a block diagram in FIG. 12. Furthermore, in the configuration in FIG. 12, the same reference numeral and the same terminology will be given to a configuration having the same function as that of the configuration in FIG. 8, and description thereof will be appropriately omitted.

Figure 12:
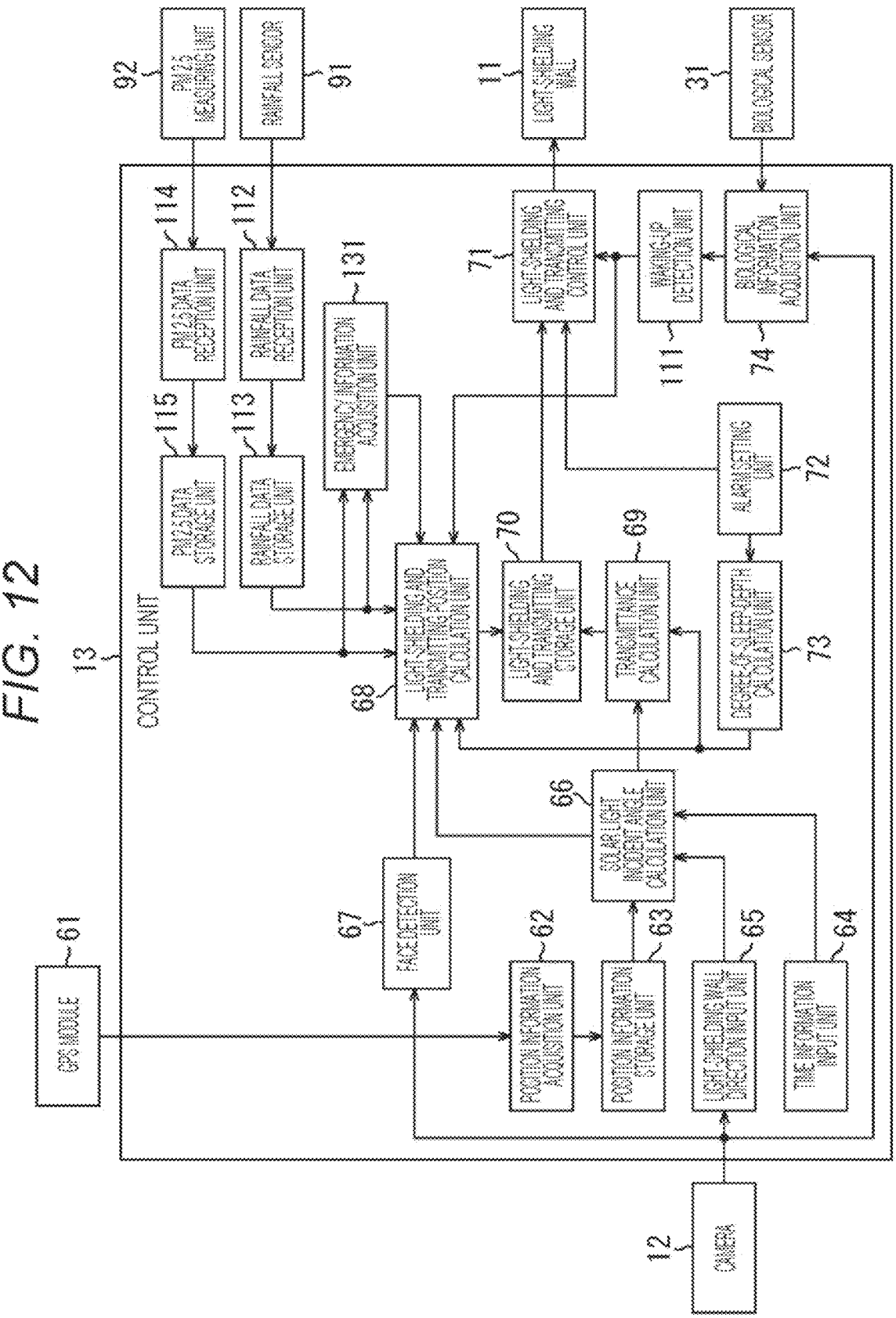
FIG. 12 is a block diagram illustrating a function of realizing the light-shielding device illustrated in FIG. 11.

Specifically, a control unit 13 in FIG. 12 is different from the control unit 13 in FIG. 8 in that an emergency information acquisition unit 131 is further provided.

The emergency information acquisition unit 131 reads out the rainfall data and the PM 2.5 data which are stored in the rainfall data storage unit 113 and the PM 2.5 data storage unit 115, and determines whether or not information is emergent information on the basis of whether or not values of the two pieces of data exceed a predetermined reference value. Then, in a case where determination is made as emergent information, the emergency information acquisition unit 131 determines the type of the emergency information and supplies the type to the light-shielding and transmitting position calculation unit 68. Furthermore, it is possible to determine emergency simply from the type of the emergent information other than determination as to whether or not a value of external information is an abnormal value.

The light-shielding and transmitting position calculation unit 68 generates light-shielding and transmitting information for controlling the light-shielding state or the transmitting state of the respective panels 21 on the basis of the emergency information so that emergency information is displayed on the entire surface of the light-shielding wall 11 as the window, and stores the information in the light-shielding and transmitting storage unit 70.

The light-shielding and transmitting control unit 71 controls the light-shielding state or the transmitting state of the respective panels 21 of the light-shielding wall 11 on the basis of the light-shielding and transmitting information stored in the light-shielding and transmitting storage unit 70 to display the emergency information on the entire surface of the light-shielding wall 11 as the window.

<Emergency Information Display Processing>

Figure 13:
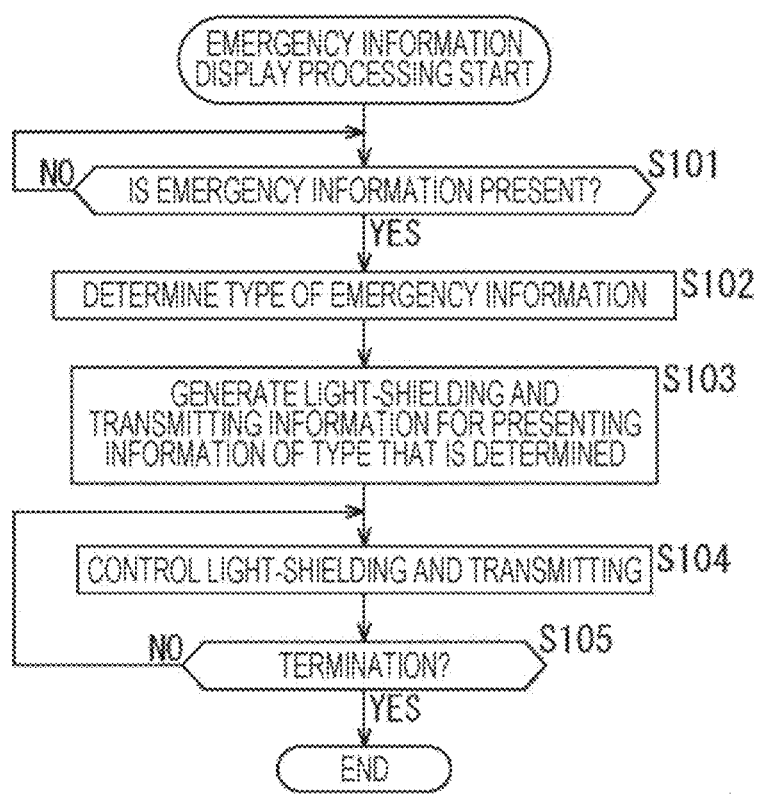
FIG. 13 is a flowchart illustrating emergent information display processing by the light-shielding device illustrated in FIG. 11.

Next, emergency information display processing in the control unit 13 of the light-shielding device illustrated in FIG. 12 will be described with reference to a flowchart in FIG. 13.

In step S101, the emergency information acquisition unit 131 reads out the rainfall data and the PM 2.5 data which are stored in the rainfall data storage unit 113 and the PM 2.5 data storage unit 115, and determines whether or not emergency information is present on the basis of whether or not a value of at least one of the two pieces of data exceeds a predetermined reference value. In a case where it is determined that emergency information is not present, similar processing is repeated.

Then, in step S101, in a case where it is determined that a value of at least one of the rainfall data and the PM 2.5 data is an abnormal value exceeding the predetermined reference value, and emergency information is present, the processing proceeds to step S102.

In step S102, the emergency information acquisition unit 131 determines at least the type of data that is an abnormal value between the rainfall data and the PM 2.5 data, and notifies the light-shielding and transmitting position calculation unit 68 of the type.

In step S103, the light-shielding and transmitting position calculation unit 68 reads out information of the designated type between the rainfall data and the PM 2.5 data, generates light-shielding and transmitting information for controlling light-shielding or transmitting of the respective panels 21 of the light-shielding wall 11 to display the information of the designated type on the entirety of the light-shielding wall 11, and stores the light-shielding and transmitting information in the light-shielding and transmitting storage unit 70.

In step S104, the light-shielding and transmitting control unit 71 controls light-shielding or transmitting of the respective panels 21 of the light-shielding wall 11 on the basis of the light-shielding and transmitting information to display emergency information indicating heavy rainfall as illustrated at the right portion in FIG. 11, or measurement of PM 2.5 in an abnormal amount as illustrated at the left portion in FIG. 11 as an example.

According to the above-described processing, when an abnormal value is detected in the amount of rainfall or PM 2.5, it is possible to rapidly present the abnormal value.

Furthermore, when the processing is set to independent processing taking priority over the above-described comfortable waking-up control processing, display of emergency information can be preferentially performed, and it is possible to present emergency to a user in a more rapidly. In addition, description has been given of an example in which only an abnormal value of the amount of rainfall or PM 2.5 is displayed. However, external information may be acquired over the Internet or the like, and occurrence of earthquake, tidal waves, and the like may be displayed on the light-shielding wall 11.

5. Fourth Embodiment

Description has been given of an example in which information on the light-shielding wall 11 in a visual line direction at timing at which comfortable waking-up is encouraged or waking-up is detected in correspondence with the biological information, and an example in which the emergency information is presented, but the light-shielding wall 11 may be allowed to function as a timer in correspondence with the biological information as an example.

Figure 14:
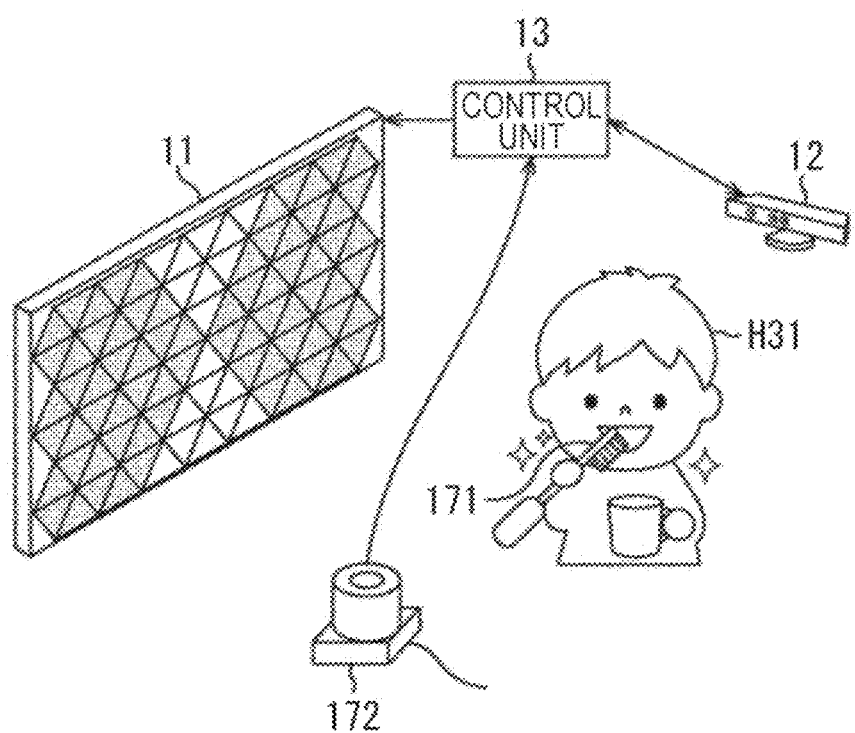
FIG. 14 is a view illustrating a configuration example of a fourth embodiment of the light-shielding device according to the present disclosure.

Specifically, for example, in a case where the light-shielding wall 11 is provided in the vicinity of a washroom, as illustrated in FIG. 14, the control unit 13 detects timing at which a user H31 takes out an electric toothbrush 171 from a charging stand 172 as biological information at which brushing of teeth (so-called toothbrushing) by a user H31 is initiated. Then, the control unit 13 expresses information indicating a brushing elapse time from the timing at which the biological information indicating initiation of the brushing of teeth is detected by controlling the light-shielding state or the transmitting state of the panels 21 of the light-shielding wall 11, thereby allowing the light-shielding wall 11 to function as a timer. Furthermore, FIG. 14 illustrates an example in which the transmitting state and the light-shielding state of triangular panels 21 in the light-shielding wall 11 are controlled to use a plurality of the panels 21 in a mosaic shape, and thus a timer shape resembling a sandglass is displayed.

When the user brushes teeth by setting a timer elapse time displayed on the light-shielding wall 11 resembling the mosaic sandglass to a standard, it is possible to secure appropriate brushing time.

Furthermore, FIG. 14 illustrates an example in which the panels 21 of the light-shielding wall 11 have a triangular shape, but shapes other than the triangular shape are also possible. The other shapes are also possible as long as an elapsed time as a timer is likely to be visually recognized.

In addition, the biological information indicating timing at which brushing of teeth is initiated may be timing other than the timing at which the electric toothbrush 171 is taken out from the charging stand 172. For example, the biological information may be timing at which the user carries the electric toothbrush 171 which is determined from an image captured by the camera 12, or may be a combination thereof.

A method of determining whether or not brushing of teeth is initiated by using an image can also correspond to a toothbrush that is not electric toothbrush.

<Configuration Example for Realizing Light-Shielding Device Illustrated in FIG. 14>

Next, a configuration example for realizing the light-shielding device illustrated in FIG. 14 will be described with reference to a block diagram in FIG. 15. Furthermore, the configuration of the light-shielding wall 11 and the camera 12 is similar to the configuration in FIG. 1, and thus description thereof will be omitted.

Figure 15:
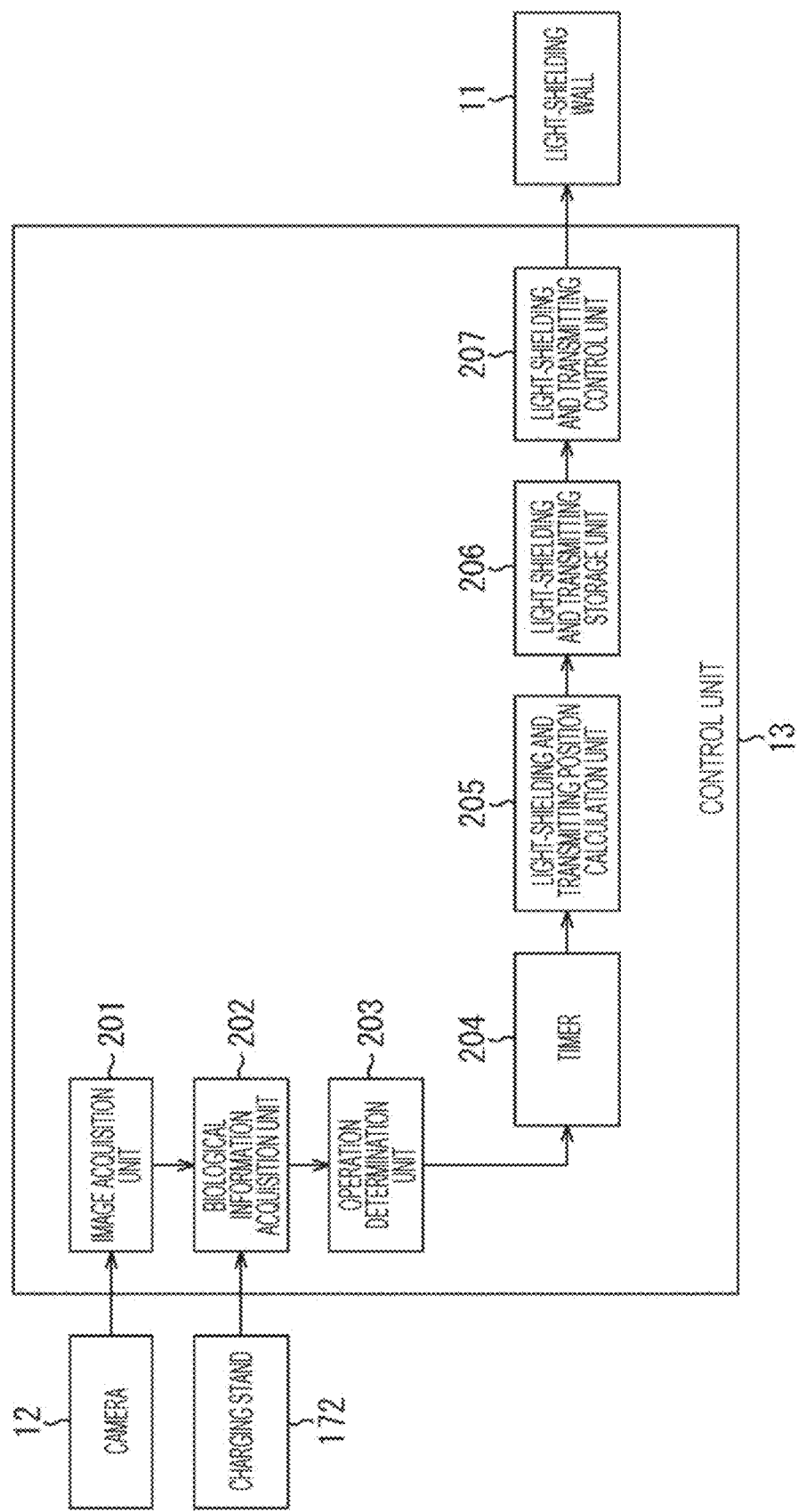
FIG. 15 is a block diagram illustrating a function of realizing the light-shielding device illustrated in FIG. 14.

A control unit 13 in FIG. 15 includes an image acquisition unit 201, a biological information acquisition unit 202, an operation determination unit 203, a timer 204, a light-shielding and transmitting position calculation unit 205, a light-shielding and transmitting storage unit 206, and a light-shielding and transmitting control unit 207. Furthermore, the light-shielding and transmitting storage unit 206 and the light-shielding and transmitting control unit 207 are basically the same as the light-shielding and transmitting storage unit 70 and the light-shielding and transmitting control unit 71, and thus description thereof will be appropriately omitted.

The image acquisition unit 201 acquires an image captured by the camera 12, and supplies the image to the biological information acquisition unit 202.

The biological information acquisition unit 202 acquires the image supplied from the image acquisition unit 201 as biological information, and determines whether or not a user takes out and uses the electric toothbrush 171. In addition, the biological information acquisition unit 202 determines whether or not the electric toothbrush 171 in a state of being taken out and used on the basis of a charging state of the charging stand 172. Then, the biological information acquisition unit 202 supplies the determination results to the operation determination unit 203 as biological information.

The operation determination unit 203 determines whether or not brushing is initiated on the basis of the determination results. Specifically, for example, use of the electric toothbrush 171 is recognized from at least one of the determination results, the operation determination unit 203 regards that brushing is initiated, and initiates an operation of the timer 204.

The timer 204 supplies information of a count value that is counted for a predetermined setting time to the light-shielding and transmitting position calculation unit 205.

The light-shielding and transmitting position calculation unit 205 is basically the same as the light-shielding and transmitting position calculation unit 68. However, here, the light-shielding and transmitting position calculation unit 205 generates light-shielding and transmitting information for controlling light-shielding and transmitting of the respective panels 21 of the light-shielding wall 11 to be displayed in a shape that is likely to be visually recognized as a timer that resembles, for example, a sandglass or the like at a predetermined position on the light-shielding wall 11, and stores the information in the light-shielding and transmitting storage unit 206.

<Timer Display Processing by Light-Shielding Device Illustrated in FIG. 15>

Figure 16:
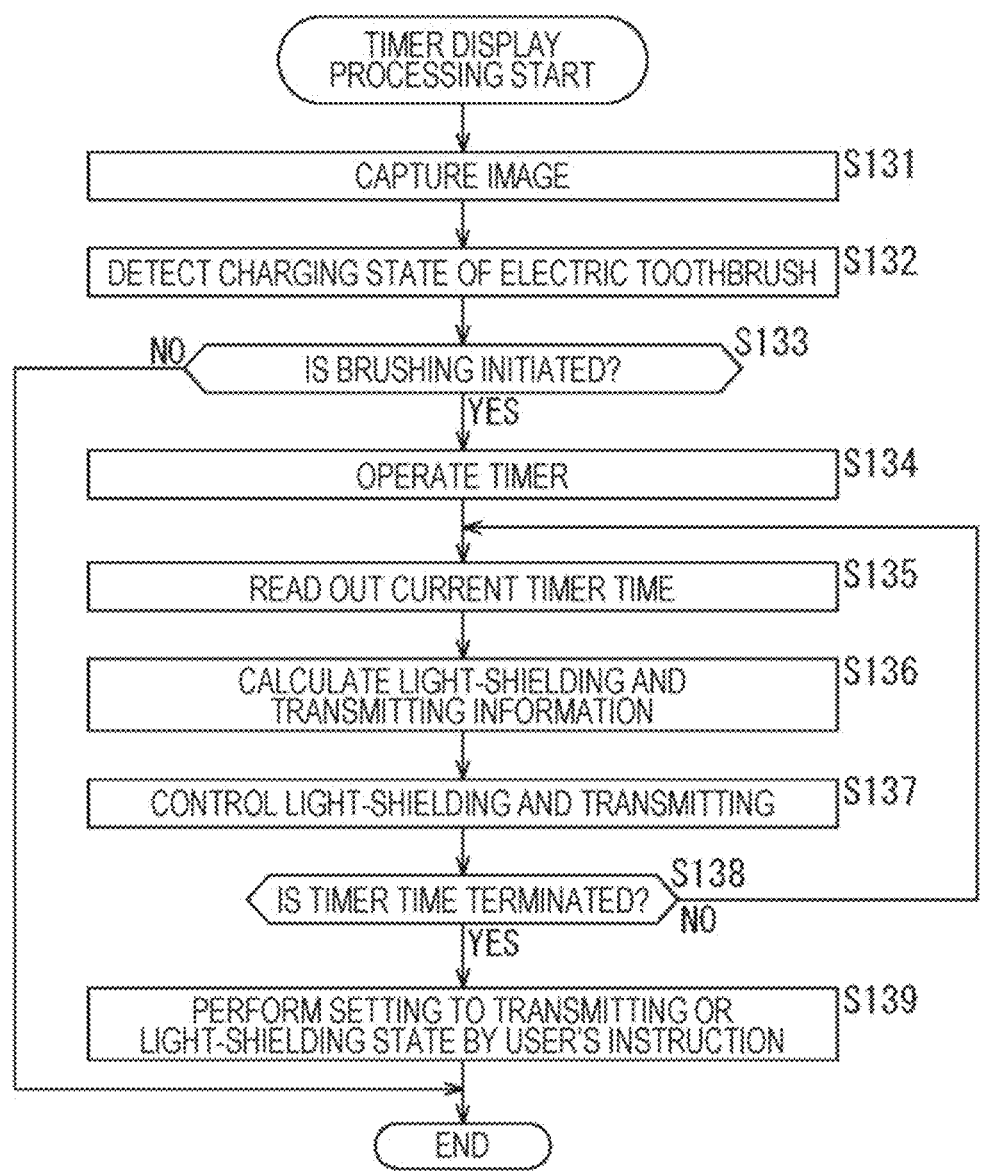
FIG. 16 is a flowchart illustrating timer display processing by the light-shielding device illustrated in FIG. 14.

Next, timer display processing in the control unit 13 of the light-shielding device illustrated in FIG. 15 will be described with reference to a flowchart in FIG. 16.

In step S131, the biological information acquisition unit 202 acquires a user image captured by the camera 12 from the image acquisition unit 201 as biological information. At this time, the biological information acquisition unit 202 determines whether or not the user in the image as the biological information grips the electric toothbrush 171, and supplies the determination result to the operation determination unit 203.

In step S132, the biological information acquisition unit 202 detects information as to whether or not the electric toothbrush 171 is connected to the charging stand 172 and is chargeable as biological information, determines whether or not the electric toothbrush 171 is taken out from the charging stand 172 and is used, and supplies the determination result to the operation determination unit 203.

In step S133, the operation determination unit 203 determines whether or not the user initiates brushing on the basis of the determination result, which is transmitted from the biological information acquisition unit 202, based on the biological information. More specifically, in a case where it is determined that the electric toothbrush 171 is used in at least any one of the determination result based on the image as the biological information and the determination result based on the charging state of the charging stand 172 as the biological information, the operation determination unit 203 regards that use of brushing is initiated. In this case, the processing proceeds to step S134.

In step S134, the operation determination unit 203 initiates count of the timer 204.

In step S135, the timer 204 supplies a count value that is counted to the light-shielding and transmitting position calculation unit 205.

In step S136, the light-shielding and transmitting position calculation unit 205 generates light-shielding and transmitting information for controlling the light-shielding state or the transmitting state of the respective panels 21 of the light-shielding wall 11 to be displayed as a timer, for example, in a shape resembling a sandglass on the basis of the count value supplied from the timer 204, and stores the light-shielding and transmitting information in the light-shielding and transmitting storage unit 206.

In step S137, the light-shielding and transmitting control unit 207 controls the light-shielding state or the transmitting state of the respective panels 21 of the light-shielding wall 11 on the basis of the light-shielding and transmitting information stored in the light-shielding and transmitting control unit 206.

In step S138, the light-shielding and transmitting position calculation unit 205 determines whether or not count by the timer is terminated, and in a case where it is determined that the count is not terminated, the processing returns to step S135. That is, the processing in steps S135 to S137 is repeated until count by the timer 204 is terminated, and the light-shielding state or the transmitting state of the panels 21 of the light-shielding wall 11 is controlled in correspondence with a sequential variation of the count value. Accordingly, display of the timer in a shape that resembles a sandglass continues while varying in accordance with the elapse of time.

Then, in step S138, when count of the timer 204 is terminated, the processing proceeds to step S139.

In step S138, the light-shielding and transmitting control unit 206 controls the respective panels 21 of the light-shielding wall 11 to the light-shielding state or the transmitting state in a state that is set in advance, and the processing is terminated.

Furthermore, in step S133, in a case where it is considered that brushing by the electric toothbrush 171 is not initiated, the processing proceeds to step S138.

According to the above-described processing, a determination is made as to whether or not the user initiates brushing of teeth using the electric toothbrush 171 on the basis of the biological information, and in a case where it is determined that brushing is initiated, a timer indicating an elapsed time from initiation of brushing is displayed on the light-shielding wall 11. Accordingly, it is possible to realize appropriate brushing of teeth.

Furthermore, description has been given of an example in which initiation of brushing of teeth is detected on the basis of the biological information, and a timer is displayed from a detection timing. However, an application may be made to a timer for other activities as long as initiation of any activity by a user can be detected as biological information and an elapsed time from an initiation timing can be presented. For example, the light-shielding wall 11 may be set as a window of a bath room, a water level of a bathtub in bathing may be measured as biological information, in a case where the water level is rapidly raised, it may be regarded that a user initiates bathing in the bathtub, and an elapsed time from a bathing initiation timing may be displayed as a timer on the window as the light-shielding wall 11. However, in this case, the respective panels 21 of the light-shielding wall 11 are set to a state like frosted glass even in the transmitting state. Further, description has been given of an example in which display is performed in a shape that resembles a sandglass, but the timer may be displayed in a shape that resembles other objects.

6. Fifth Embodiment

Description has been given of an example in which the light-shielding wall 11 is allowed to function as a timer in correspondence with the biological information. However, the light-shielding wall 11 may be used as a wall surface that separates a conference room and a passage. When the conference room is used, the light-shielding wall 11 may be set to the light-shielding state to be used as a wall of the conference room, as it is close to expiration of a use time of the conference room, a transmitting region may be gradually widened, and at a termination timing, the entirety of the light-shielding wall 11 may be set to the transmitting state.

Figure 17:
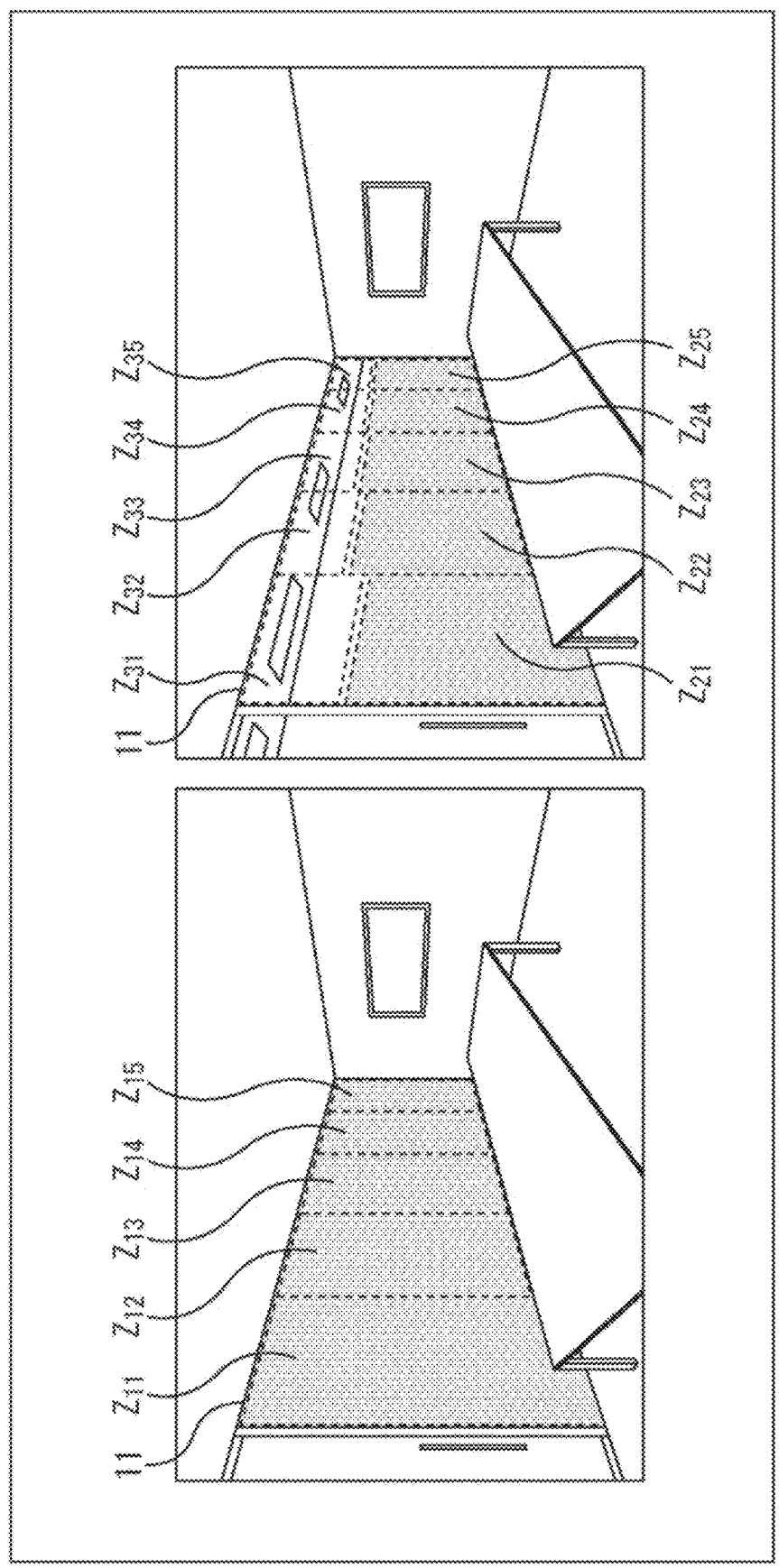
FIG. 17 is a view illustrating a fifth embodiment of the light-shielding device according to the present disclosure.

That is, as illustrated at the left portion in FIG. 17, a wall that becomes a boundary between a conference room (inside thereof) on the right side in the drawing and a passage (outside of the conference room) on the left side in the drawing is constituted by the light-shielding wall 11, and in a state of being used as the conference room, the entirety of regions Z11 and Z15 of the light-shielding wall 11 are set to the light-shielding state. Then, as it is close to an expiration time of a use time of the conference room, as illustrated at the right portion in FIG. 17, the regions Z11 to Z15 constituted by panels 21, which are controlled to the light-shielding state, of the light-shielding wall 11 include regions Z31 to Z35 constituted by panels 21 which are controlled to the transmitting state and regions Z21 to Z25 constituted by panels 21 which are controlled to the light-shielding state. Further, control is performed as follows. With the passage of time, the regions Z31 to Z35 constituted by the panels 21 controlled to the transmitting state broaden downward in the drawing, and the entirety of regions of the light-shielding wall 11 become the regions Z31 to Z35 constituted by the panels 21 which are controlled to the transmitting state at the expiration time.

Figure 18:
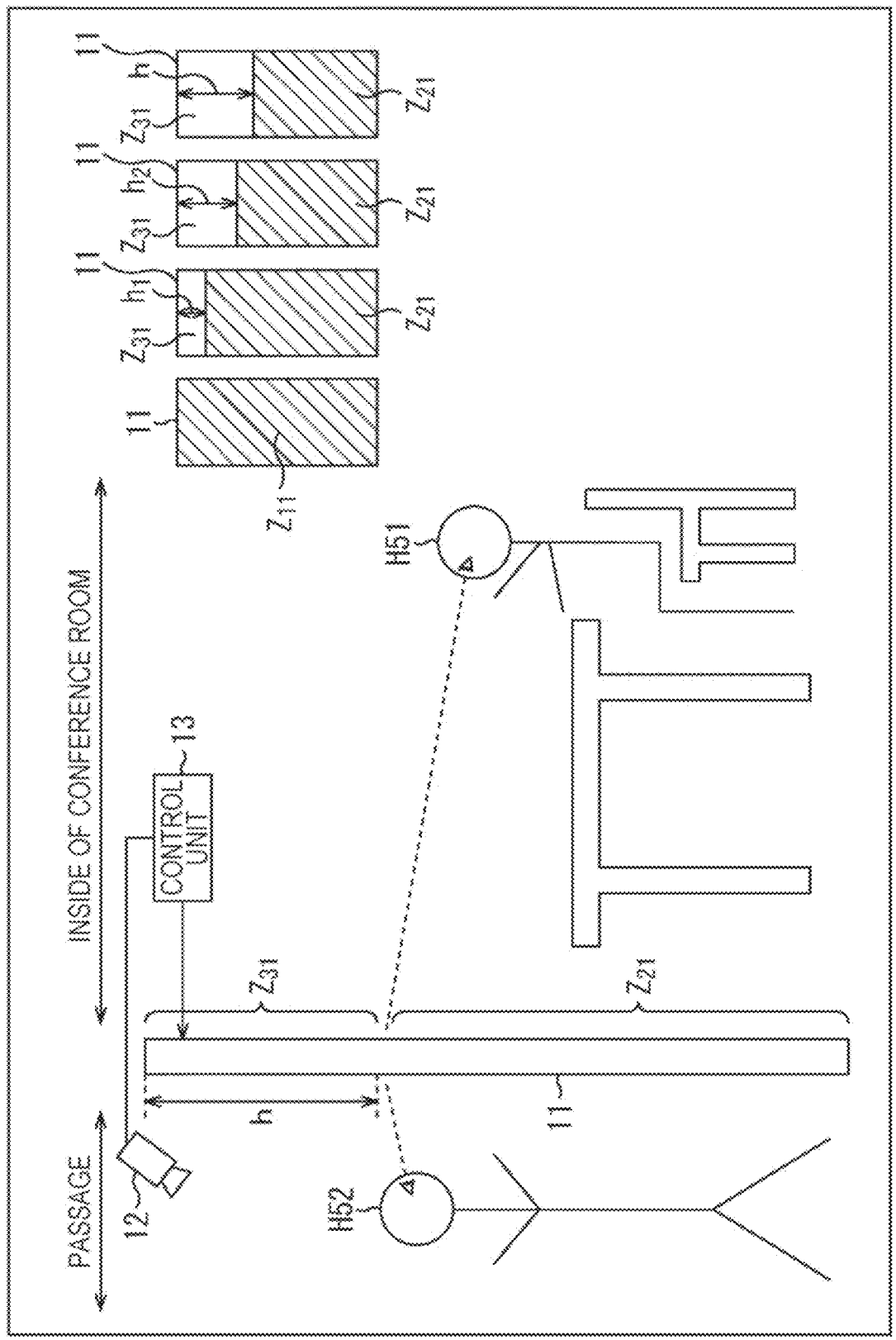
FIG. 18 is a view illustrating a configuration example of the light-shielding device illustrated in FIG. 17.

At this time, as illustrated in FIG. 18, the control unit 13 acquires information of the height of a pedestrian H52, which is obtained from a depth image captured by the camera 12 provided on a passage side, as biological information, and the pedestrian H52 is not permitted to visually recognize a user H51 in the conference room in a conference room using time in consideration of the height of the pedestrian H52.

Furthermore, FIG. 18 illustrates a relationship between the passage and the conference room with the light-shielding wall 11 at the right portion in FIG. 17 set as a boundary, and is a vertical cross-sectional view of a portion corresponding to the regions Z21 and Z31.

Specifically, the control unit 13 obtains a height h of the region Z31 higher than the height of the pedestrian H52 in the light-shielding wall 11 on the basis of the information of the height of the pedestrian H52. As it is close to an expiration time of the conference room use time, as illustrated at an upper-right portion in FIG. 18, with the passage of time, the control unit 13 performs setting to the region Z11 of which entire surface is in the light-shielding state, setting to the region Z31 that has the height h1 and is in the transmitting state and the region Z21 that is in the light-shielding state at the subsequent timing, setting to the region Z31 that has a height h2 (>h1) and is in the transmitting state and the region Z21 that is in the light-shielding state at the subsequent timing, and setting to the region Z31 that has a height h and is in the transmitting state and the region Z21 that is in the light-shielding state at a point of time that is the expiration time in time series from the left side to the right side.

According to the control, a user who uses the conference room can recognize that it is close to the expiration time of the conference room use time due to an increase of the region, which is in the transmitting state, of the light-shielding wall 11. At this time, until the expiration time, the pedestrian H52 on the passage side cannot visually recognize the inside of the conference room that is meant to be invisible by the user H51, and thus the user can comfortably use the conference room. In addition, after the expiration time of the conference room use time, it enters a state in which the pedestrian H52 on the passage side can visually recognize the inside of the conference room, and thus it is possible to encourage the user of the conference room to terminate use of the conference room.

<Configuration Example for Realizing Light-Shielding Device Illustrated in FIG. 17 and FIG. 18>

Next, a configuration for realizing the light-shielding device illustrated in FIG. 17 and FIG. 18 will be described with reference to a block diagram in FIG. 19. Furthermore, the configuration of the light-shielding wall 11 and the camera 12 is similar to the configuration in FIG. 1, and thus description thereof will be omitted.

Figure 19:
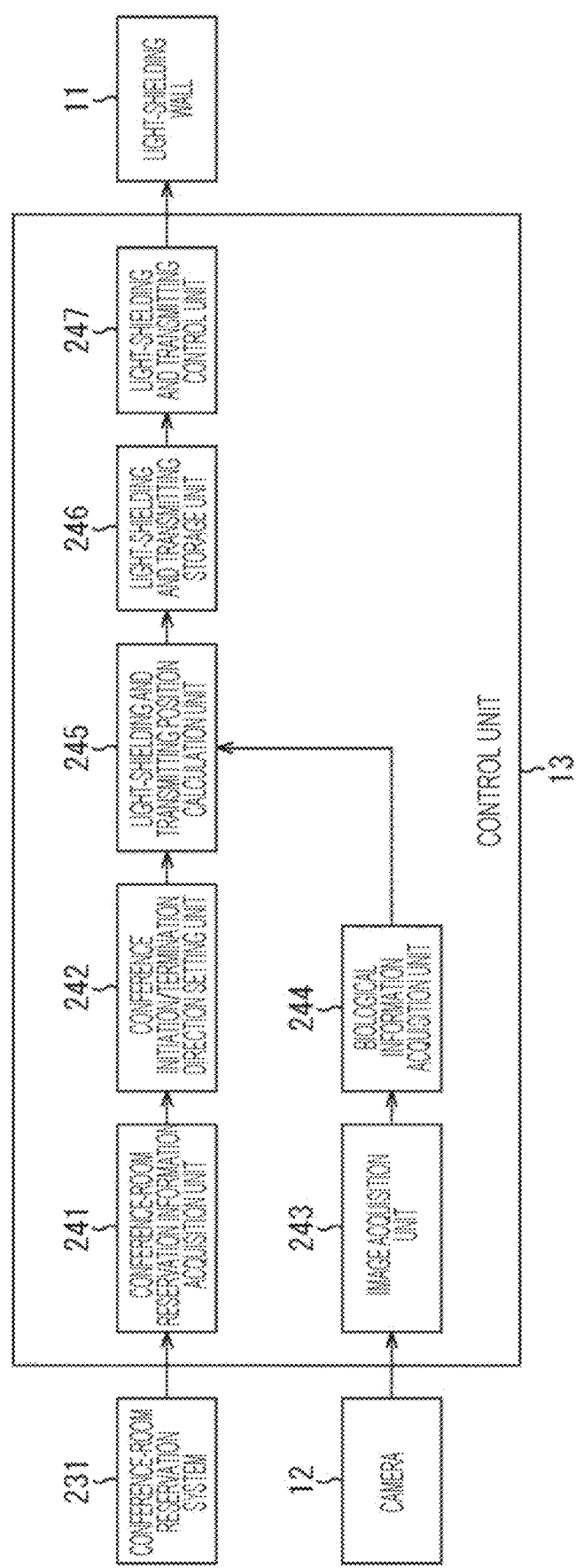
FIG. 19 is a block diagram illustrating a function of realizing the light-shielding device illustrated in FIG. 17 and FIG. 18.

A control unit 13 in FIG. 19 includes a conference-room reservation information acquisition unit 241, a conference initiation/termination direction setting unit 242, an image acquisition unit 243, a biological information acquisition unit 244, a light-shielding and transmitting position calculation unit 245, a light-shielding and transmitting storage unit 246, and a light-shielding and transmitting control unit 247. Furthermore, the light-shielding and transmitting storage unit 246 and the light-shielding and transmitting control unit 247 are basically the same as the light-shielding and transmitting storage unit 70 and the light-shielding and transmitting control unit 71, and thus description thereof will be appropriately omitted.

The conference-room reservation information acquisition unit 241 acquires conference-room reservation information of a conference room, in which the control unit 13 is provided, from a conference-room reservation system 231 that is provided at the outside and accepts reservation of the conference room, and supplies the information to the conference initiation/termination direction setting unit 242.

The conference initiation/termination direction setting unit 242 instructs the light-shielding and transmitting position calculation unit 245 to perform direction at a conference-room use initiation time and direction from time previous to an expiration time by a predetermined time on the basis of the conference-room reservation information. More specifically, the conference initiation/termination direction setting unit 242 instructs the light-shielding and transmitting position calculation unit 245 to perform direction for setting the entirety of the panels 21 of the light-shielding wall 11 to the light-shielding state at the conference-room use initiation time. In addition, the conference initiation/termination direction setting unit 242 instructs the light-shielding and transmitting position calculation unit 245 to broaden a region constituted by panels 21 in the transmitting state in time series and gradually from a timing previous to the use expiration time by a predetermined time to the expiration time, and to set the entirety of the panels 21 to the transmitting state after the expiration time.

The image acquisition unit 243 acquires a depth image of the pedestrian H52 which is captured by the camera 12 provided at the passage, and supplies the depth image to the biological information acquisition unit 244.

The biological information acquisition unit 244 acquires the height of the pedestrian H52 from the depth image as biological information, and supplies the biological information to the light-shielding and transmitting position calculation unit 245.

The light-shielding and transmitting position calculation unit 245 controls light-shielding or transmitting of the panels 21 of the light-shielding wall 11 in correspondence with the direction that given in the instruction from the conference initiation/termination direction setting unit 242. At this time, in the direction up to the expiration time of the conference room, the light-shielding and transmitting position calculation unit 245 gradually broadens a range in the transmitting state so that the pedestrian H52 cannot visually recognize the inside of the conference room on the basis of the information of the height of the pedestrian H52 which is transmitted from the biological information acquisition unit 244.

<Conference-Room Remaining Time Notification Processing by Light-Shielding Device Illustrated in FIG. 17 and FIG. 18>

Figure 20:
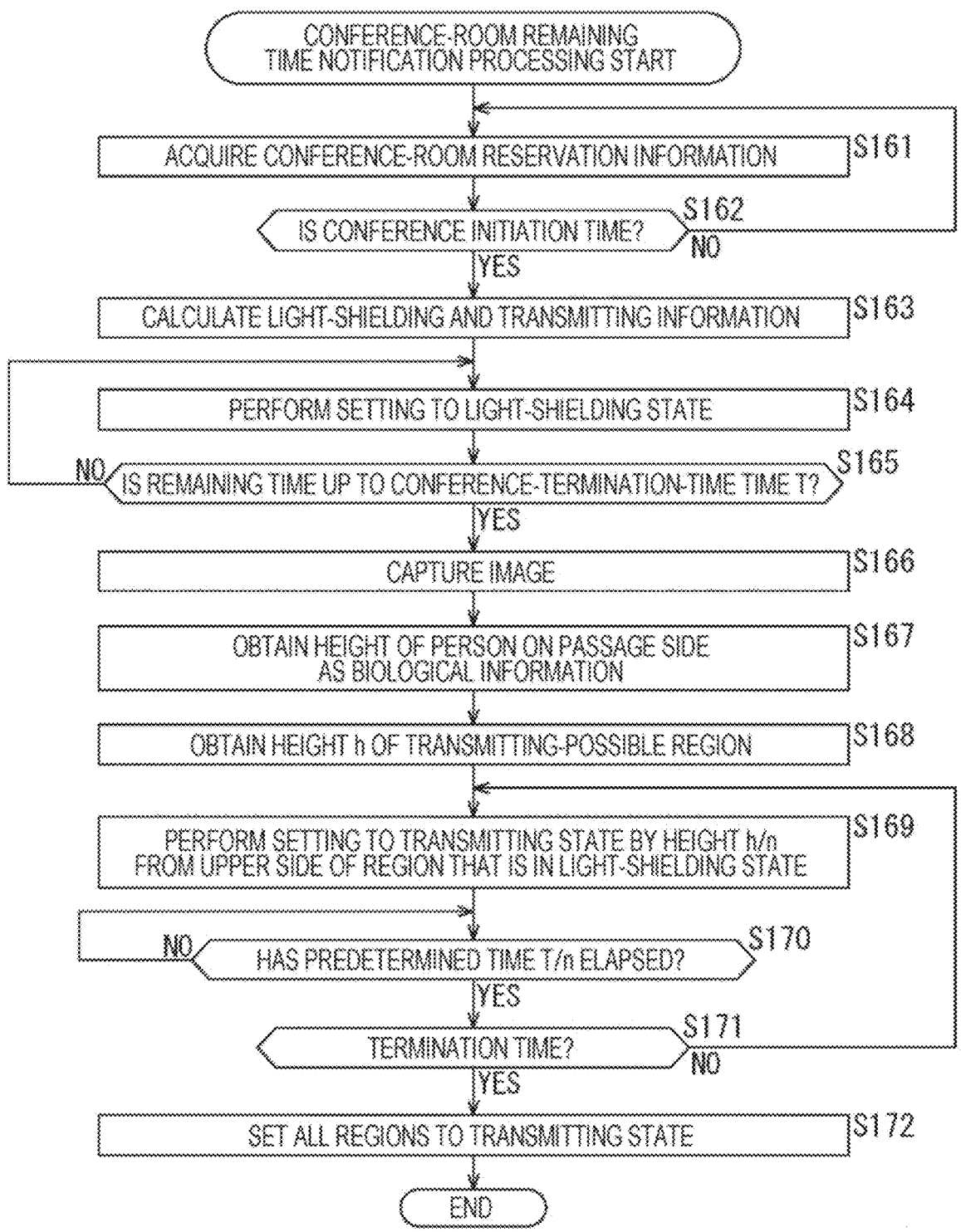
FIG. 20 is a flowchart illustrating conference-room remaining time notification processing by the light-shielding device illustrated in FIG. 17 and FIG. 18.

Next, conference-room remaining time notification processing in the control unit 13 of the light-shielding device illustrated in FIG. 17 and FIG. 18 will be described with reference to a flowchart in FIG. 20.

In step S161, the conference-room reservation information acquisition unit 241 acquires reservation information including a use initiation time and a use expiration time of a conference room, in which the conference-room reservation information acquisition unit 241 is provided, from the conference-room reservation system 231, and supplies the reservation information to the conference initiation/termination direction setting unit 242.

In step S162, the conference initiation/termination direction setting unit 242 determines whether or not the current time is the use initiation time of the conference room on the basis of the reservation information, and repeats similar processing until the current time is determined as the initiation time. In step S162, in a case where it is determined that it reaches the initiation time, the processing proceeds to step S163.

In step S163, the conference initiation/termination direction setting unit 242 instructs the light-shielding and transmitting position calculation unit 245 to perform direction at initiation of the conference room. According to the instruction, the light-shielding and transmitting position calculation unit 245 generates light-shielding and transmitting information for controlling the entirety of the panels 21 of the light-shielding wall 11 to the light-shielding state as direction of the conference-room initiation time, and stores the information in the light-shielding and transmitting storage unit 246.

In step S164, the light-shielding and transmitting control unit 247 controls the respective panels 21 of the light-shielding wall 11 on the basis of the light-shielding and transmitting information stored in the light-shielding and transmitting storage unit 246, and shields the entirety of the panels 21.

In step S165, the conference initiation/termination direction setting unit 242 determines whether or not a current remaining time up to the expiration time of the conference room is time T, and in a case where it is determined that the remaining time is not the time T, the processing returns to step S164. That is, the processing in steps S164 and S165 is repeated until the remaining time becomes the time T, and the entirety of the panels 21 of the light-shielding wall 11 are continuously set to the light-shielding state.

In step S165, in a case where the current remaining time up to the expiration time of the conference room is determined as the time T, the processing proceeds to step S166.

In step S166, the image acquisition unit 243 acquires a depth image that is captured by the camera 12 and includes the pedestrian H52 on the passage side, and supplies the depth image to the biological information acquisition unit 244. At this time, the conference initiation/termination direction setting unit 242 instructs the light-shielding and transmitting position calculation unit 245 to perform direction for displaying a remaining time up to a use expiration time of the conference room.

In step S167, the biological information acquisition unit 244 obtains the height of the pedestrian H52 from the depth image that is acquired, and supplies the height to the light-shielding and transmitting position calculation unit 245 as biological information.

In step S168, the light-shielding and transmitting position calculation unit 245 calculates the height h in FIG. 18, which can be set to the transmitting state in the light-shielding wall 11, from the height of the light-shielding wall 11 and the height of the pedestrian H52.

In step S169, the light-shielding and transmitting position calculation unit 245 generates light-shielding and transmitting information for setting a region, which is lower than the height of the immediately previous light-shielding region by h/n, to the transmitting state, and stores the information in the light-shielding and transmitting storage unit 246. According to this, the light-shielding and transmitting control unit 247 controls the respective panels 21 of the light-shielding wall 11 on the basis of the light-shielding and transmitting information stored in the light-shielding and transmitting storage unit 246 to set the region, which is lower than the height of the immediately previous light-shielding region by h/n, to the transmitting state. Furthermore, here, n is the number of division steps, is the number of times of changing the height of the region in the transmitting state within the time T, and can be arbitrarily set.

In step S170, the light-shielding and transmitting position calculation unit 245 determines whether or not a predetermined time T/n has elapsed, and repeats similar processing until the predetermined time T/n has elapsed. Then, in step S170, in a case where it is determined that the predetermined time T/n has elapsed, the processing proceeds to step S171.

In step S171, the light-shielding and transmitting position calculation unit 245 determines whether or not it reaches the expiration time of the conference room, and in a case where it is determined that it does not reach the expiration time, the processing returns to step S169. That is, the processing from step S169 to step S171 is repeated until it reaches the expiration time of the conference room use time, and processing for setting a region of the panels 21 in the light-shielding state to the transmitting state by height h/n from an upper side is repeated at a predetermined time interval T/n. Then, in step S171, in a case where it is determined that it does not reach the expiration time of the conference room, the processing proceeds to step S172.

In step S172, the light-shielding and transmitting control unit 246 controls the entirety of the panels 21 of the light-shielding wall 11 to the transmitting state, and the processing is terminated.

According to the above-described processing, when it reaches the use initiation time of the conference room, the entirety of the light-shielding wall 11 is set to the light-shielding state, and thus it is possible to allow the use to recognize that use as the conference room is possible.

In addition, an upper side that is set to the light-shielding state is changed into the transmitting state by the height h/n from timing previous to the expiration time by the time T at a predetermined time interval T/n, and a transmitting region is gradually broadened. Accordingly, it is possible to notify a user of the conference room of a situation in which it is close to the expiration time of the use time.

At this time, a range of the transmitting region within the conference room use time is set on the basis of the height of the pedestrian 52 on the passage side as the biological information, and thus it is possible to notify the user of the situation in which it is close to the expiration time of the conference room while reliably preventing the pedestrian from visually recognizing the inside of the conference room.

Further, when the expiration time of the conference room use time has elapsed, the entirety of the light-shielding wall 11 is controlled to the transmitting state, and thus it is possible to notify the user of the conference room of the expiration time, and it is possible to encourage termination of the use of the conference room.

Furthermore, description has been given of an example in which the remaining time of the conference room use time is given in notification. However, the above-described configuration is applicable to a space other than the conference room as long as the space is occupied and used in accordance with time. For example, the above-described configuration is also used in a room such as a rehearsal studio, a karaoke box, and the like which are paid by the hour can also be used in a similar manner.

In addition, in a case where a pedestrian does not exist on the passage side, the height of the pedestrian as the biological information may be set to 0, and the height h may be set to the height of the light-shielding wall 11 as is. Further, in a case where a plurality of pedestrians exist, the height of the tallest pedestrian among the plurality of pedestrians may be used as the biological information.

<Example of Execution by Software>

The above-described series of processing can be executed by hardware, but can be executed by the software. In a case where the series of processing is executed by software, a program that constitutes the software is installed from a recording medium in a computer provided with exclusive hardware, a general-purpose personal computer to which various programs are installed to execute various functions, and the like.

Figure 21:
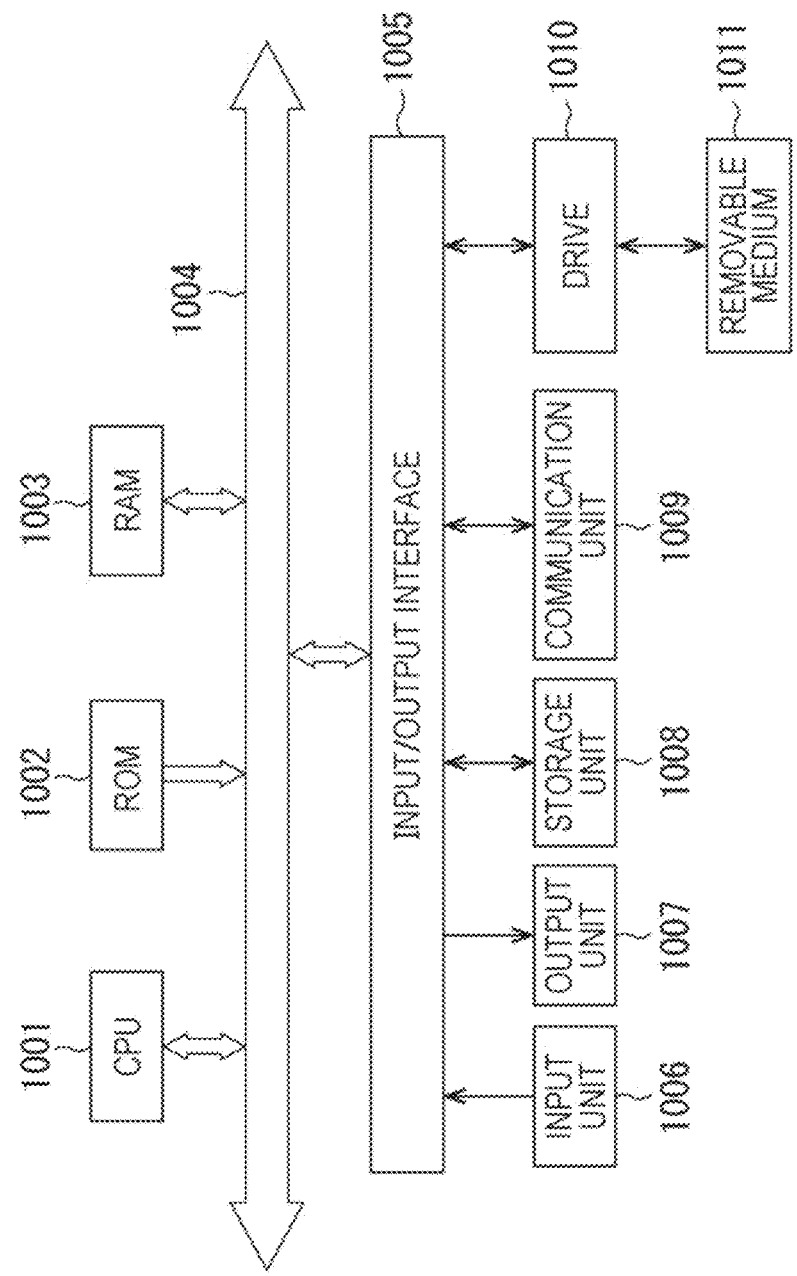
FIG. 21 is a view illustrating a configuration example of a general-purpose personal computer.

FIG. 21 illustrates a configuration example of the general-purpose personal computer. The personal computer is provided with a central processing unit (CPU) 1001. An input/output interface 1005 is connected to the CPU 1001 through a bus 1004. A read only memory (ROM) 1002 and a random access memory (RAM) 1003 are connected to the bus 1004.

An input unit 1006 including an input device such as a keyboard and a mouse which are used to input an operation command by a user, an output unit 1007 that outputs a processing operation screen or a processing result image to a display device, a storage unit 1008 such as a hard disc drive that stores a program or various pieces of data, and a communication unit 1009 that includes a local area network (LAN) adapter and the like, and executes communication processing through a network represented by the Internet are connected to the input/output interface 1005. In addition, a drive 1010 that performs reading/writing of data with respect to a removable medium 1011 such as a magnetic disk (including a flexible disk), an optical disc (including a compact disc-read only memory (CD-ROM) and a digital versatile disc (DVD)), a magneto-optical disc (including a mini disc (MD)), and a semiconductor memory is connected to the input/output interface 1005.

The CPU 1001 executes various kinds of processing in accordance with programs which are stored in the ROM 1002, or programs which are read out from the removable medium 1011 such as the magnetic disk, the optical disc, the magneto-optical disc, and the semiconductor memory, are installed in the storage unit 1008, and are loaded from the storage unit 1008 into the RAM 1003. Data necessary for execution of the various kinds of processing by the CPU 1001, or the like is also appropriately stored in the RAM 1003.

In the computer having the above-described configuration, the CPU 1001 loads a program stored, for example, in the storage unit 1008 into the RAM 1003 through the input/output interface 1005 and the bus 1004 and executes the program, whereby the above-described series of processing is performed.

The program that is executed by the CPU 1001 can be provided in a state of being recorded, for example, on the removable medium 1011 as a package medium or the like. In addition the program can be provided through a wired or wireless transmission medium such as a local area network, the Internet, and digital satellite broadcasting.

In the computer, the programs can be installed in the storage unit 1008 through the input/output interface 1005 when the removable medium 1011 is mounted in the drive 1010. In addition, the programs can be installed in the storage unit 1008 after being received by the communication unit 1009 through the wired or wireless transmission medium. In addition, the programs can be installed in the ROM 1002 or the storage unit 1008 in advance.

Furthermore, the CPU 1001 in FIG. 21 is, for example, the control unit 13 in FIG. 5. The CPU 1001 accepts the position information supplied from the GPS module 61 and an input of the depth image supplied from the camera 12 through the input unit 1006, receives the biological information transmitted from the biological sensor 31 through the communication unit 1009, and executes the above-described series of processing. Then, the CPU 1001 outputs a signal for controlling the light-shielding wall 11 from the output unit 1007.

In addition, the programs which are executed by the computer may be programs in which processing is performed in time series according to the procedure described in this specification, or may be programs in which processing is performed in parallel or at a necessary timing such as when a call is made.

Further, in this specification, the system represents an assembly of a plurality of constituent elements (devices, modules (parts), and the like), and whether or not the entirety of the constituent elements exist in the same casing does not matter. Accordingly, all of a plurality of devices which are accommodated in individual casings and are connected through a network, and one device in which a plurality of modules are accommodated in one casing represent the system.

Furthermore, an embodiment of the present disclosure is not limited to the above-described embodiments, and various modifications can be made in a range not departing from the gist of the present disclosure.

For example, the present disclosure can have a cloud computing configuration in which one function is shared by a plurality of devices and is processed in cooperation through a network.

In addition, the respective steps described in the flowchart can be executed in a state of being shared by a plurality of devices in addition to execution by one device.

Further, in a case where a plurality of kinds of processing are included in one step, the plurality of kinds of processing included in one step can be executed in a state of being shared by a plurality of devices in addition to execution by one device.

Furthermore, the present disclosure can employ the following configurations.

<1> A light-shielding device including:

a light-shielding wall that partitions a first space and a second space and includes a plurality of regions capable of being controlled to a transmitting state in which light is transmitted or a light-shielding state in which light is shielded;

a light-shielding and transmitting information generation unit that generates light-shielding and transmitting information for controlling the transmitting state or the light-shielding state of a position of each of the plurality of regions on the basis of biological information of a user; and a control unit that controls the transmitting state or the light-shielding state of the plurality of regions of the light-shielding wall on the basis of the light-shielding and transmitting information generated by the light-shielding and transmitting information generation unit.

<2> The light-shielding device according to <1>, in which the light-shielding wall is a window that separates an interior and an exterior, the light-shielding device further includes a biological information acquisition unit that acquires biological information indicating whether or not the user is sleeping in an interior, and the light-shielding and transmitting information generation unit generates light-shielding and transmitting information for controlling the transmitting state or the light-shielding state of the position of each of the plurality of regions to irradiate a specific position of the interior with light from a light source that exists in the exterior on the basis of whether or not the user is sleeping which is acquired by the biological information acquisition unit.

<3> The light-shielding device according to <2>, in which the biological information further includes information indicating an orientation of a user's face in sleep, and in a case where the user sets an alarm time as an alarm, the light-shielding and transmitting information generation unit generates light-shielding and transmitting information for controlling the transmitting state or the light-shielding state of the position of each of the plurality of regions on the basis of the orientation of the user's face in sleep on the basis of the biological information so that the user's eyes located at the specific position of the interior are irradiated with light of which a light source is the sun, which is light from the light source that exists in the exterior, at the alarm time.

<4> The light-shielding device according to <3>, in which the biological information further includes information for obtaining a sleep state of the user, the light-shielding device further includes, a solar light incident angle calculation unit that calculates an incident angle of light, which is incident to each of the regions of the light-shielding wall and of which a light source is the sun, as a solar light incident angle on the basis of information of latitude and longitude as a position of the solar light incident angle calculation unit, an orientation of the light-shielding wall, and time information, and a degree-of-sleep-depth calculation unit that determines whether or not the user is sleeping at time near the alarm time on the basis of biological information that indicates whether or not the user is sleeping in the interior and is used to obtain a sleep state of the user, and further obtains an easily waking-up time at which the depth of sleep is shallow in a case where it is determined that the user is sleeping, and the light-shielding and transmitting information generation unit generates light-shielding and transmitting information for controlling the transmitting state or the light-shielding state of a position of each of the plurality of regions on the basis of biological information that is information indicating the orientation of the user's face in sleep, and the solar light incident angle information so that the user's eyes are irradiated with light of which a light source is the sun at easily waking-up time which corresponds to the alarm time and at which the depth of sleep is shallow.

<5> The light-shielding device according to <4>, in which the biological information for obtaining the sleep state of the user includes information of a pulse rate, a body temperature, a blood pressure, a breathing frequency, and a body turning frequency of the user.

<6> The light-shielding device according to <5>, further including:

an image capturing unit that captures an image of the user who is sleeping, in which the biological information acquisition unit acquires information of the body turning frequency as the biological information as the biological information on the basis of the image captured by the image capturing unit.

<7> light-shielding device according to <1>, further including:

an external information acquisition unit that acquires external information; and a waking-up detection unit that detects waking-up of the user after the alarm time on the basis of biological information for obtaining a sleep state of the user, and in a case where waking-up is detected after the alarm time by the waking-up detection unit, the light-shielding and transmitting information generation unit generates light-shielding and transmitting information for controlling the transmitting state or the light-shielding state of a position of each of the plurality of regions so that the user is capable of visually recognizing display based on the external information.

<8> The light-shielding device according to <7>, in which the external information acquisition unit acquires external information including rainfall data based on the amount of rainfall that is measured by a rainfall sensor, or PM 2.5 data that is a measurement amount of PM 2.5 that is measured by a PM 2.5 measuring device, and in a case where waking-up is detected by the waking-up detection unit, the light-shielding and transmitting information generation unit generates light-shielding and transmitting information for controlling the transmitting state or the light-shielding state of the position of each of the plurality of regions on the basis of an orientation of the user's face so that the user is capable of visually recognizing display corresponding to measurement results which correspond to the rainfall data and the PM 2.5 data as the external information.

<9> The light-shielding device according to <7>, in which the light-shielding and transmitting information generation unit generates light-shielding and transmitting information for controlling the transmitting state or the light-shielding state of the position of each of the plurality of regions so that the user is capable of visually recognizing the display based on the external information at a position on the light-shielding wall at which light from a light source that exists in the exterior does not become backlight for the user.

<10> The light-shielding device according to <7>, further including:

an abnormality determination unit that determines whether or not the external information indicates an abnormal state, in which in correspondence with a determination by the abnormality determination unit as to whether or not the external information is abnormal, the light-shielding and transmitting information generation unit generates light-shielding and transmitting information for controlling the transmitting state or the light-shielding state of the position of each of the plurality of regions so that the display based on the external information is displayed on the light-shielding wall at a different position or in a different size.

<11> The light-shielding device according to <4>, further including:

a transmittance setting unit that sets a transmittance in the plurality of regions controlled to the transmitting state in the light-shielding and transmitting information on the basis of the solar light incident angle information so as to adjust a light quantity of light of which a light source is the sun that is visually recognized by the user, and adds the transmittance to the light-shielding and transmitting information.

<12> The light-shielding device according to <1>, further including:

a biological information acquisition unit that acquires biological information indicating initiation of a predetermined activity of the user, in which the light-shielding and transmitting information generation unit generates light-shielding and transmitting information for controlling the transmitting state or the light-shielding state of a position of each of the plurality of regions so that the user is capable of visually recognizing an elapsed time from timing at which the predetermined activity of the user, which is acquired by the biological information acquisition unit, is initiated.

<13> The light-shielding device according to <12>, in which the biological information acquisition unit acquires biological information indicating initiation of brushing of teeth as the biological information indicating that the predetermined activity of the user is initiated, and the light-shielding and transmitting information generation unit generates light-shielding and transmitting information for controlling the transmitting state or the light-shielding state of the position of each of the plurality of regions so that the user is capable of visually recognizing an elapsed time from timing at which brushing of teeth of the user is initiated and which is acquired by the biological information acquisition unit in a shape that resembles a sandglass.

<14> The light-shielding device according to <12>, further including:

an image capturing unit that captures an image of a user; and a charging stand of an electric toothbrush that is used in brushing of teeth of the user, in which the biological information acquisition unit determines whether or not the user grips the toothbrush in an image that is captured by the image capturing unit, determines whether or not the electric toothbrush is connected to the charging stand and is capable of being charged, and acquires biological information indicating initiation of the brushing of teeth in at least one of a case where the electric toothbrush is gripped by the user, and a case where the electric toothbrush is not connected to the charging stand and is not capable of being charged in the image on the basis of the determination result.

<15> The light-shielding device according to <1>, in which the first space is an interior, the second space is an exterior, and the light-shielding wall is a wall that separates the interior and the exterior, the light-shielding device further includes a biological information acquisition unit that acquires the height of a person who exists in the exterior as biological information, the light-shielding and transmitting information generation unit generates light-shielding and transmitting information for controlling the entirety of the plurality of regions to a light-shielding state at an initiation time of a usable time of the interior, and the light-shielding and transmitting information generation unit generates light-shielding and transmitting information for controlling the plurality of regions higher than the height among the plurality of regions in the light-shielding wall to the transmitting state on the basis of information of the height of a person which is acquired by the biological information acquisition unit at time previous to an expiration time of the interior usable time by a predetermined time.

<16> The light-shielding device according to <15>, in which after the time that is previous to the expiration time of the interior usable time by a predetermined time, the light-shielding and transmitting information generation generates light-shielding and transmitting information for controlling the plurality of regions, which are higher than the height and are controlled to a light-shielding state in the light-shielding wall, among the plurality of regions to the transmitting state in a time series or gradually in an order from the plurality of regions of the highest partial regions on the basis of the information of the height of a person which is acquired by the biological information acquisition unit.

<17> The light-shielding device according to <15>, in which at the expiration time of the interior usable time, the light-shielding and transmitting information generation unit generates light-shielding and transmitting information for controlling the entirety of the plurality of regions to the transmitting state.

<18> The light-shielding device according to <15>, in which the interior includes a conference room, and an interior of a room that is paid by the hour.

<19> A light-shielding method of a light-shielding device including a light-shielding wall that partitions a first space and a second space and includes a plurality of regions capable of being controlled to a transmitting state in which light is transmitted or alight-shielding state in which light is shielded, the method including steps of:

generating light-shielding and transmitting information for controlling the transmitting state or the light-shielding state of a position of each of the plurality of regions on the basis of biological information of a user; and controlling the transmitting state or the light-shielding state of the plurality of regions of the light-shielding wall on the basis of the light-shielding and transmitting information that is generated.

<20> A program that allows a computer to function as:

a light-shielding wall that partitions a first space and a second space and includes a plurality of regions capable of being controlled to a transmitting state in which light is transmitted or a light-shielding state in which light is shielded;

a light-shielding and transmitting information generation unit that generates light-shielding and transmitting information for controlling the transmitting state or the light-shielding state of a position of each of the plurality of regions on the basis of biological information of a user; and a control unit that controls the transmitting state or the light-shielding state of the plurality of regions of the light-shielding wall on the basis of the light-shielding and transmitting information generated by the light-shielding and transmitting information generation unit.

REFERENCE SIGNS LIST

11 Light-shielding wall
12, 12-1, 12-2 Camera
13 Control unit
21, 21-A to 21-C, 21-1, 21-2, 21' Panel
31 Biological sensor
61 GPS
62 Position information acquisition unit
63 Position information storage unit
64 Time information input unit
65 Light-shielding wall direction input unit
66 Solar light incident angle calculation unit
67 Face diction unit
68 Light-shielding and transmitting position calculation unit
69 Transmittance calculation unit
70 Transmitting and light-shielding storage unit
71 Light-shielding and transmitting control unit
72 Alarm setting unit
73 Degree-of-sleep-depth calculation unit
74 Biological information acquisition unit
91 Rainfall sensor
92 PM 2.5 measuring unit
111 Waking-up detection unit
112 Rainfall data reception unit
113 Rainfall data storage unit
114 PM 2.5 data reception unit
115 PM 2.5 data storage unit
131 Emergency information acquisition unit
171 Electric toothbrush
172 Charging stand
201 Image acquisition unit
202 Biological information acquisition unit
203 Operation determination unit
204 Timer
205 Light-shielding and transmitting position calculation unit
206 light-shielding and transmitting storage unit
207 light-shielding and transmitting control unit
231 Conference-room reservation system
241 Conference-room reservation state
242 conference initiation/termination direction setting unit
243 Image acquisition unit
244 Biological information acquisition unit
245 Light-shielding and transmitting position calculation unit
246 Light-shielding and transmitting storage unit
247 Light-shielding and transmitting control unit

The invention claimed is:

1. A light-shielding device, comprising:
a light-shielding wall that partitions a first space and a second space, wherein
the light-shielding wall includes a plurality of regions, and
each region of the plurality of regions is configured to operate in one of a transmitting state in which light is transmitted or a light-shielding state in which the light is shielded; and
a processor configured to:
generate light-shielding and transmitting information based on biological information of a user, wherein the biological information includes at least one of a pulse rate, a body temperature, a blood pressure, a breathing frequency, a body turning frequency, a height, or an orientation of a face of the user; and
control, based on the generated light-shielding and transmitting information, each region of the plurality of regions to operate in one of the transmitting state or the light-shielding state.

2. The light-shielding device according to claim 1, wherein
the first space is an interior of a third space,
the second space is an exterior of the third space,
the light-shielding wall is a window that separates the interior of the third space and the exterior of the third space, and
the processor is further configured to:
acquire the biological information that indicates whether the user is in a sleep state in the interior;
generate the light-shielding and transmitting information based on the biological information that indicates whether the user is in the sleep state in the interior; and
control, based on the generated light-shielding and transmitting information, each region of the plurality of regions to irradiate a position of the interior with the light from a light source in the exterior.

3. The light-shielding device according to claim 2, wherein
in a case where the user sets an alarm time as an alarm, the processor is further configured to:
generate the light-shielding and transmitting information based on the orientation of the face of the user in the sleep state; and
control, based on the generated light-shielding and transmitting information, each region of the plurality of regions to irradiate eyes of the user located at the position of the interior with the light of the light source at the alarm time, wherein the light source is the sun.

4. The light-shielding device according to claim 3, wherein
the biological information further includes information associated with the sleep state of the user,
the processor is further configured to:
calculate an incident angle of the light incident to each region of the plurality of regions of the light-shielding wall as a solar light incident angle based on information of latitude and longitude as a position of the processor, an orientation of the light-shielding wall, and time information;
determine whether the user is in the sleep state at a time in proximity to the alarm time based on the biological information that indicates whether the user is in the sleep state in the interior;
obtain, based on the determination whether the user is in the sleep state, waking-up time at which a degree of depth of sleep is smaller than a threshold; and
generate, based on information that indicates the orientation of the face of the user in the sleep state, and information associated with the solar light incident angle, light-shielding and transmitting information to irradiate the eyes of the user with the light of the sun at the waking-up time, and
the waking-up time corresponds to the alarm time.

5. The light-shielding device according to claim 4, further comprising an imaging device configured to capture an image of the user in the sleep state, wherein the processor is further configured to acquire information of the body turning frequency as the biological information based on the captured image.

6. The light-shielding device according to claim 4, wherein the processor is further configured to:
set a transmittance in the plurality of regions and transmitting information based on information associated with the solar light incident angle, to adjust a light quantity of the light of the light source; and
add the transmittance to the light-shielding and transmitting information.

7. The light-shielding device according to claim 1, wherein the processor is further configured to:
acquire external information;
detect a waking-up action of the user after an alarm time based on the biological information; and
in a case where the waking-up action is detected after the alarm time, generate the light-shielding and transmitting information based on the external information.

8. The light-shielding device according to claim 7, wherein
the external information includes one of rainfall data based on an amount of rainfall that is measured by a rainfall sensor, or PM 2.5 data that is a measurement amount of PM 2.5 that is measured by a PM 2.5 measuring device, and
in a case where the waking-up action is detected, the processor is further configured to generate the light-shielding and transmitting information based on the orientation of the face of the user and the external information.

9. The light-shielding device according to claim 7, wherein
the processor is further configured to generate, based on the external information, the light-shielding and transmitting information such that display corresponding to measurement results associated with the external information is recognizable at a position on the light-shielding wall.

10. The light-shielding device according to claim 7, wherein the processor is further configured to:
determine whether the external information indicates a specific state, wherein the specific state indicates a specific amount of the rainfall or a specific value of the PM 2.5 data; and
generate, based on the determination whether the external information indicates the specific state, the light-shielding and transmitting information such that display corresponding to measurement results associated with the external information is displayed on the light-shielding wall at a specific position or in a specific size.

11. The light-shielding device according to claim 1, wherein the processor is further configured to:
acquire the biological information that indicates initiation of an activity of the user; and
generate the light-shielding and transmitting information based on the biological information that indicates the initiation of the activity of the user.

12. The light-shielding device according to claim 11, wherein
the initiation of brushing of teeth indicates the initiation of the activity of the user.

13. The light-shielding device according to claim 11, further comprising:
an imaging device configured to capture an image of the user; and
a charging stand of an electric toothbrush that is used in brushing of teeth of the user, and
wherein the processor is further configured to:
determine whether the user grips the electric toothbrush in the captured image;
determine whether the electric toothbrush is connected to the charging stand; and
acquire biological information that indicates initiation of the brushing of teeth in at least one of a case where the electric toothbrush is gripped by the user or a case where the electric toothbrush is not connected to the charging stand in the captured image.

14. The light-shielding device according to claim 1, wherein
the first space is an interior of a third space,
the second space is an exterior of the third space,
the light-shielding wall is a wall that separates the interior and the exterior, and
the processor is further configured to:
acquire a height of a person who exists in the exterior as the biological information;
generate the light-shielding and transmitting information to control the plurality of regions to the light-shielding state at an initiation time of an interior usable time; and
generate the light-shielding and transmitting information to control a first set of regions of the plurality of regions higher than the height in the light-shielding wall to the transmitting state, based on information of the height of the person at a time previous to an expiration time of the interior usable time by a specific time.

15. The light-shielding device according to claim 14, wherein
after the time that is previous to the expiration time of the interior usable time by the specific time, the processor is further configured to generate the light-shielding and transmitting information to control a second set of regions of the plurality of regions, which are higher than the height and are controlled to the light-shielding state in the light-shielding wall, to the transmitting state in a time series.

16. The light-shielding device according to claim 14, wherein
at the expiration time of the interior usable time, the processor is further configured to generate the light-shielding and transmitting information to control the plurality of regions to the transmitting state.

17. The light-shielding device according to claim 14, wherein the interior includes a conference room.

18. A light-shielding method, comprising:
in a light-shielding device including a light-shielding wall that partitions a first space and a second space, wherein the light-shielding wall includes a plurality of regions, and each region of the plurality of regions is configured to operate in one of a transmitting state in which light is transmitted or a light-shielding state in which the light is shielded,
generating light-shielding and transmitting information based on biological information of a user, wherein the biological information includes at least one of a pulse rate, a body temperature, a blood pressure, a breathing frequency, a body turning frequency, a height, or an orientation of a face of the user; and
controlling, based on the generated light-shielding and transmitting information, each region of the plurality of regions to operate in one of the transmitting state or the light-shielding state.

19. A non-transitory computer-readable medium having stored thereon, computer-executable instructions which, when executed by a computer, cause the computer to execute operations, the operations comprising:
generating light-shielding and transmitting information based on biological information of a user, wherein the biological information includes at least one of a pulse rate, a body temperature, a blood pressure, a breathing frequency, a body turning frequency, a height, or an orientation of a face of the user; and
controlling, based on the generated light-shielding and transmitting information, each region of a plurality of regions of a light-shielding wall to operate in one of a transmitting state or a light-shielding state, wherein
the light-shielding wall partitions a first space and a second space,
the light-shielding wall includes a plurality of regions, and
each region of the plurality of regions is configured to operate in one of the transmitting state in which light is transmitted or the light-shielding state in which the light is shielded.

* * * * *